(12) United States Patent
Walker et al.

(10) Patent No.: US 8,603,094 B2
(45) Date of Patent: Dec. 10, 2013

(54) MINIMALLY INVASIVE SURGICAL TOWER ACCESS DEVICES AND RELATED METHODS

(75) Inventors: John Lawrence Walker, Madison, MS (US); John Franklin Cummins, Kosciusko, MS (US)

(73) Assignee: Spinal USA, Inc., Parsippany, NJ (US)

( * ) Notice: Subject to any disclaimer, the term of this patent is extended or adjusted under 35 U.S.C. 154(b) by 503 days.

(21) Appl. No.: 12/843,839

(22) Filed: Jul. 26, 2010

(65) Prior Publication Data

US 2012/0022594 A1 Jan. 26, 2012

(51) Int. Cl.
*A61B 17/70* (2006.01)

(52) U.S. Cl.
USPC .................................. 606/86 A; 606/246

(58) Field of Classification Search
USPC ........................ 606/246–279, 86 A
See application file for complete search history.

(56) References Cited

U.S. PATENT DOCUMENTS

| | | | |
|---|---|---|---|
| 1,925,385 A | 9/1933 | Humes et al. | |
| 2,625,967 A | 1/1953 | Stull | |
| 4,448,191 A | 5/1984 | Rodnyansky et al. | |
| 5,092,866 A | 3/1992 | Breard et al. | |
| 5,242,443 A | 9/1993 | Kambin | |
| 5,443,467 A | 8/1995 | Biedermann et al. | |
| 5,569,248 A | 10/1996 | Mathews | |
| 5,649,931 A | 7/1997 | Bryant et al. | |
| 5,728,097 A | 3/1998 | Mathews | |
| 6,183,472 B1 | 2/2001 | Lutz | |
| 6,235,028 B1 | 5/2001 | Brumfield et al. | |
| 6,251,112 B1 | 6/2001 | Jackson | |
| 6,530,929 B1 | 3/2003 | Justis et al. | |
| 6,793,656 B1 | 9/2004 | Mathews | |

(Continued)

FOREIGN PATENT DOCUMENTS

| | | |
|---|---|---|
| WO | WO 01/28436 | 4/2001 |
| WO | WO 2005/058386 | 6/2005 |

(Continued)

OTHER PUBLICATIONS

Medtronic CD Horizon® Sextant™ System, believed to be launched in or before 2002, http://www.medtronic.com/Newsroom/ImageLibraryDetails.do?itemId=1100208127594&lang=en_US, last visited Apr. 26, 2011.

(Continued)

*Primary Examiner* — Eduardo C Robert
*Assistant Examiner* — Nicholas Plionis
(74) *Attorney, Agent, or Firm* — Knobbe, Martens, Olson & Bear, LLP.

(57) ABSTRACT

Devices and methods are provided for assisting in spinal stabilization. An access device is provided that includes an outer sleeve, inner sleeve, spring latch and lock nut. The inner sleeve includes compressible grasping elements. The access device can be coupled to a screw head by sliding the outer sleeve relative to the inner sleeve and compressing the grasping elements. The coupled access device and screw can then be delivered to a target location in a patient. After providing two or more access devices, a rod member can be delivered using a rod insertion device. The rod member can serve as a connection between the two screws, and can provide spinal stabilization. An anti-torque device and a persuading device can be used to help ensure that the rod member is placed and secured in a proper location within a patient.

20 Claims, 23 Drawing Sheets

(56) References Cited

U.S. PATENT DOCUMENTS

| | | | |
|---|---|---|---|
| 6,857,343 B1 | 2/2005 | Easterbrooks et al. | |
| 7,008,422 B2 | 3/2006 | Foley et al. | |
| 7,011,660 B2 | 3/2006 | Sherman et al. | |
| 7,160,300 B2 | 1/2007 | Jackson | |
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,282,064 B2 | 10/2007 | Chin | |
| 7,306,603 B2 | 12/2007 | Boehm et al. | |
| 7,470,279 B2 | 12/2008 | Jackson | |
| 7,491,208 B2 | 2/2009 | Pond, Jr. et al. | |
| 7,491,218 B2 | 2/2009 | Landry et al. | |
| 7,497,869 B2 | 3/2009 | Justis | |
| 7,520,879 B2 | 4/2009 | Justis et al. | |
| 7,527,638 B2 | 5/2009 | Anderson et al. | |
| 7,547,318 B2 | 6/2009 | Birkmeyer et al. | |
| 7,563,264 B2 | 7/2009 | Landry et al. | |
| 7,575,581 B2 | 8/2009 | Lovell | |
| 7,588,575 B2 | 9/2009 | Colleran et al. | |
| 7,588,588 B2 | 9/2009 | Spitler et al. | |
| 7,621,918 B2 | 11/2009 | Jackson | |
| 7,666,188 B2 | 2/2010 | Anderson et al. | |
| 7,666,189 B2 | 2/2010 | Gerber et al. | |
| 7,691,132 B2 | 4/2010 | Landry et al. | |
| 7,708,763 B2 | 5/2010 | Selover et al. | |
| 7,717,944 B2 | 5/2010 | Foley et al. | |
| 7,749,233 B2 | 7/2010 | Farr et al. | |
| 7,758,617 B2 | 7/2010 | Iott et al. | |
| 7,763,055 B2 | 7/2010 | Foley | |
| 7,776,051 B2 | 8/2010 | Colleran et al. | |
| 7,824,410 B2 | 11/2010 | Simonson et al. | |
| 7,862,587 B2 | 1/2011 | Jackson | |
| 7,862,595 B2 | 1/2011 | Foley et al. | |
| 7,867,259 B2 | 1/2011 | Foley et al. | |
| 7,914,558 B2 | 3/2011 | Landry et al. | |
| 7,985,242 B2 | 7/2011 | Forton et al. | |
| 8,066,739 B2 | 11/2011 | Jackson | |
| 8,075,592 B2 | 12/2011 | Landry et al. | |
| 8,100,915 B2 | 1/2012 | Jackson | |
| 8,100,951 B2 | 1/2012 | Justis et al. | |
| 8,105,361 B2 | 1/2012 | Anderson et al. | |
| 8,152,810 B2 | 4/2012 | Jackson | |
| 8,162,948 B2 | 4/2012 | Jackson | |
| 8,273,089 B2 | 9/2012 | Jackson | |
| 8,277,491 B2 | 10/2012 | Selover et al. | |
| 2003/0149438 A1 | 8/2003 | Nichols et al. | |
| 2004/0143265 A1 | 7/2004 | Landry et al. | |
| 2004/0147937 A1* | 7/2004 | Dunbar et al. | 606/99 |
| 2004/0267275 A1 | 12/2004 | Cournoyer et al. | |
| 2005/0021031 A1 | 1/2005 | Foley et al. | |
| 2005/0065517 A1 | 3/2005 | Chin | |
| 2005/0131421 A1 | 6/2005 | Anderson et al. | |
| 2005/0131422 A1 | 6/2005 | Anderson | |
| 2005/0154389 A1 | 7/2005 | Selover et al. | |
| 2005/0228380 A1 | 10/2005 | Moore et al. | |
| 2006/0069391 A1 | 3/2006 | Jackson | |
| 2006/0074418 A1* | 4/2006 | Jackson | 606/61 |
| 2006/0084993 A1 | 4/2006 | Landry et al. | |
| 2006/0111712 A1* | 5/2006 | Jackson | 606/61 |
| 2006/0111714 A1 | 5/2006 | Foley et al. | |
| 2006/0142761 A1 | 6/2006 | Landry et al. | |
| 2006/0200135 A1 | 9/2006 | Sherman et al. | |
| 2006/0229614 A1 | 10/2006 | Foley et al. | |
| 2006/0247630 A1 | 11/2006 | Lott et al. | |
| 2006/0264942 A1 | 11/2006 | Lim et al. | |
| 2006/0264962 A1 | 11/2006 | Chin et al. | |
| 2007/0016188 A1 | 1/2007 | Boehm et al. | |
| 2007/0016198 A1 | 1/2007 | Boehm et al. | |
| 2007/0016199 A1 | 1/2007 | Boehm et al. | |
| 2007/0078460 A1 | 4/2007 | Frigg et al. | |
| 2007/0129731 A1 | 6/2007 | Sicvol et al. | |
| 2007/0167954 A1 | 7/2007 | Sicvol et al. | |
| 2007/0185491 A1 | 8/2007 | Foley et al. | |
| 2007/0191840 A1 | 8/2007 | Pond, Jr. et al. | |
| 2007/0198015 A1 | 8/2007 | Foley et al. | |
| 2007/0213714 A1* | 9/2007 | Justis | 606/61 |
| 2007/0219554 A1 | 9/2007 | Landry et al. | |
| 2007/0219854 A1 | 9/2007 | Mueller et al. | |
| 2007/0233079 A1 | 10/2007 | Fallin | |
| 2007/0233097 A1 | 10/2007 | Anderson et al. | |
| 2007/0239159 A1 | 10/2007 | Altarac et al. | |
| 2007/0299443 A1 | 12/2007 | DiPoto et al. | |
| 2007/0299444 A1 | 12/2007 | DiPoto et al. | |
| 2008/0009864 A1 | 1/2008 | Forton et al. | |
| 2008/0015582 A1 | 1/2008 | DiPoto | |
| 2008/0039838 A1 | 2/2008 | Landry et al. | |
| 2008/0045957 A1 | 2/2008 | Landry et al. | |
| 2008/0077139 A1 | 3/2008 | Landry et al. | |
| 2008/0114403 A1 | 5/2008 | Kuester et al. | |
| 2008/0125788 A1 | 5/2008 | Cohen et al. | |
| 2008/0140120 A1 | 6/2008 | Hestad et al. | |
| 2008/0140132 A1 | 6/2008 | Perez-Cruet | |
| 2009/0228055 A1 | 9/2009 | Jackson | |
| 2009/0228056 A1 | 9/2009 | Jackson | |
| 2009/0318972 A1 | 12/2009 | Jackson | |
| 2010/0137915 A1 | 6/2010 | Anderson et al. | |
| 2011/0313477 A1* | 12/2011 | McLean et al. | 606/86 A |

FOREIGN PATENT DOCUMENTS

| | | |
|---|---|---|
| WO | WO 2005/060534 | 7/2005 |
| WO | WO 2005/072081 | 8/2005 |
| WO | WO 2006/116544 | 11/2006 |

OTHER PUBLICATIONS

K2M Serengeti® brochure © 2009, believed to be introduced in or before 2007, http://www.k2m.com/en_us/products/details/21, last visited Apr. 12, 2011.

Globus Medical Pivot® MIS System, believed to be launched in or before 2005, http://www.globusmedical.com/index.php?option=com_k2&view=item&layout=item&id=234&Itemid=312, last visited Apr. 25, 2011; Globus Prime Group, http://primegroup-india.com/globus.html, last visited Feb. 24, 2011.

DePuy Spine VIPER® 2 MIS Pedicle Screw System, believed to be launched in or before 2008, http://www.depuy.com/healthcare-professionals/product-details/viper-mis-spine-system, last visited Feb. 24, 2011, http://www.spineedu.com/MediaLibrary/ProductI mages/tabid/81/AlbumID/72/CurrentPage/1/selectedmoduleid/594/Default.aspx, last visited Feb. 24, 2011.

Alphatec Spine ILLICO® MIS Posterior Fixation System, believed to be launched in or before 2008, http://www.alphatecspine.com/products/mis/illico_mis_post.asp, last visited Feb. 24, 2011.

Zimmer PathFinder® Pedicle Screw System, http://www.zimmer.com/ctl?prcat=M6&prod=y&template=MP&action=1&op=global&id=10169&pr=Y, last updated Dec. 16, 2009, last visited Apr. 25, 2011.

Stryker MANTIS Percutaneous Pedicle Screw System, brochure available at http://whatsnewatstryker.com/aans/complex-spine/#mantis, © 2007, last visited Apr. 26, 2011.

* cited by examiner

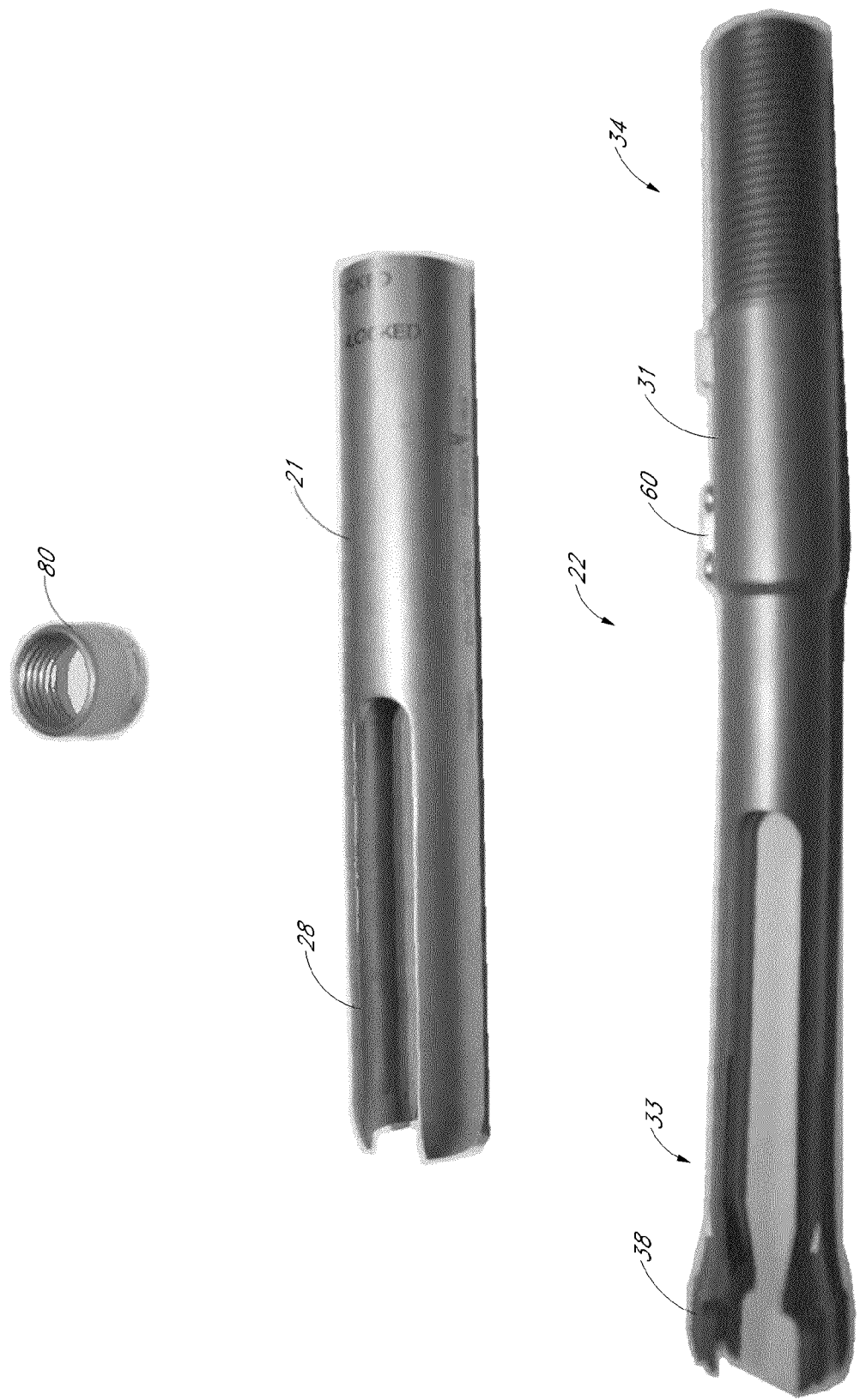

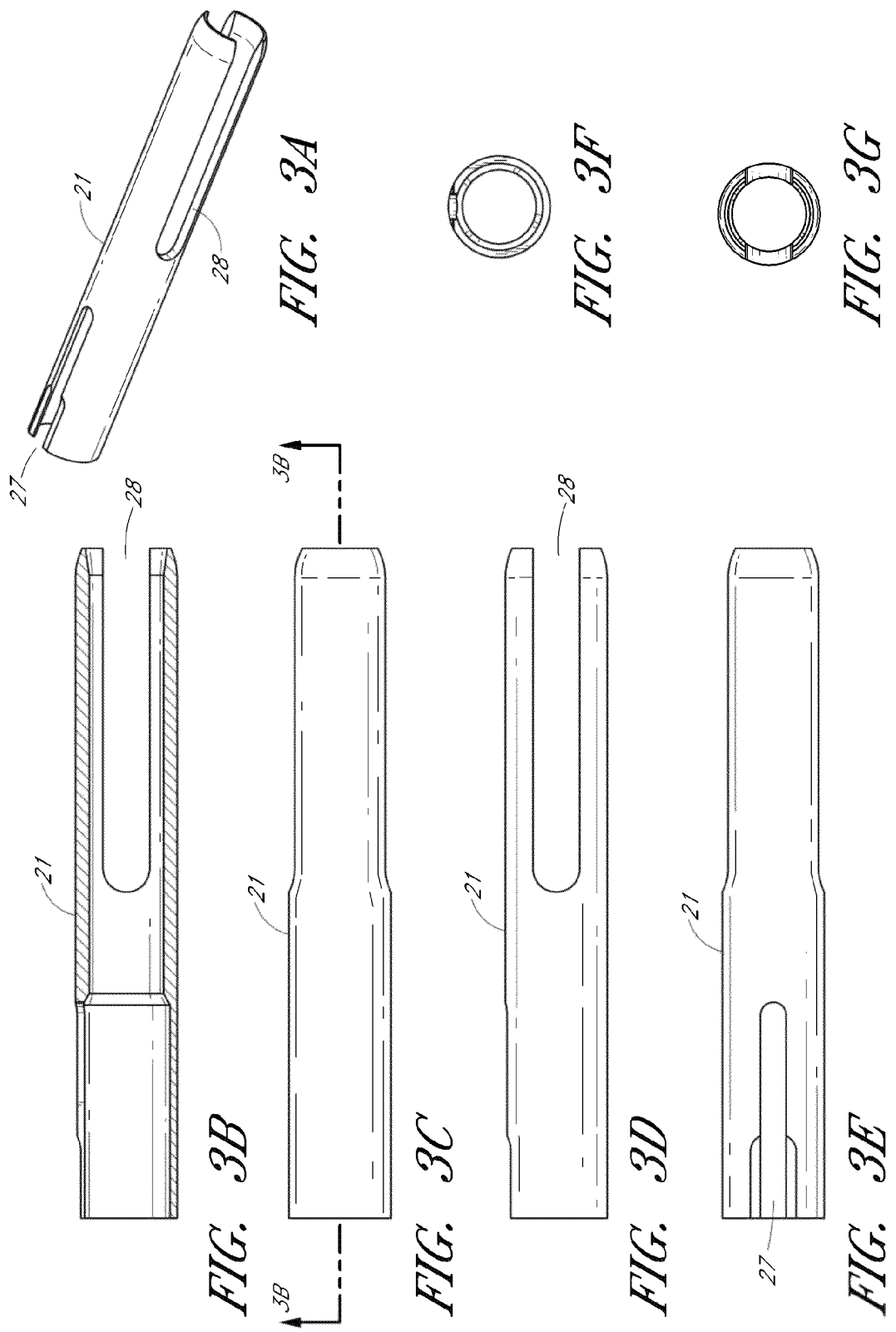

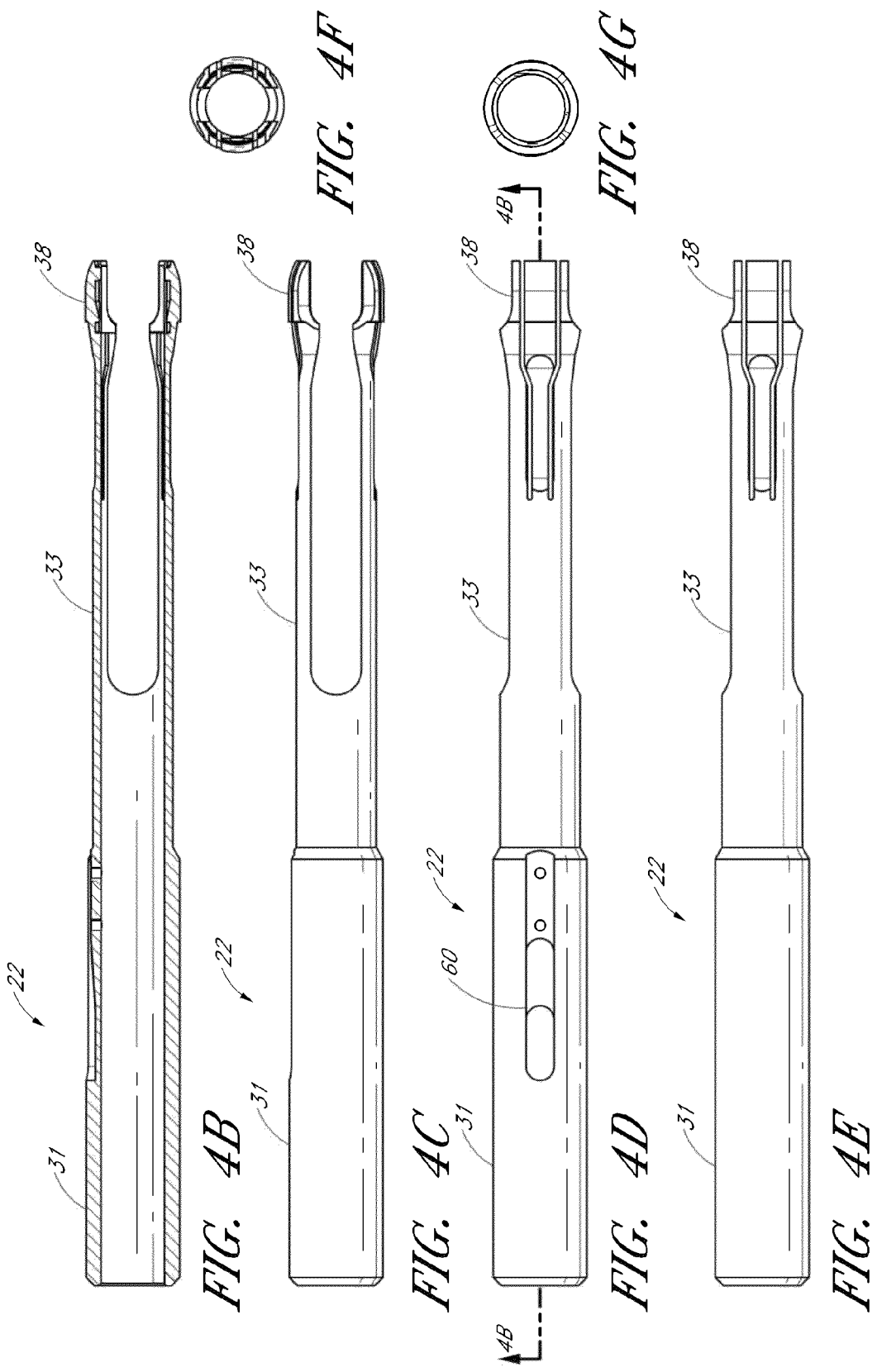

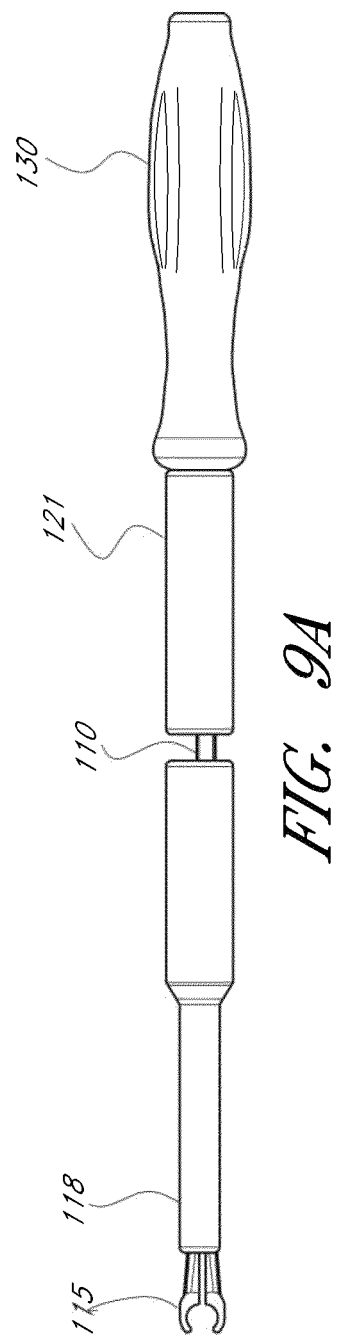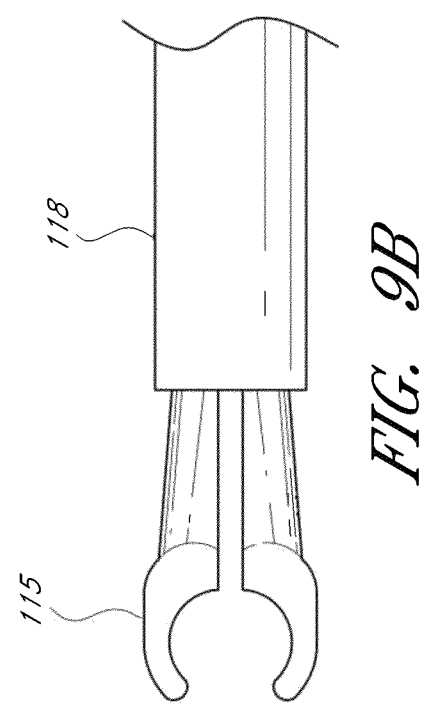
FIG. 9A
FIG. 9B

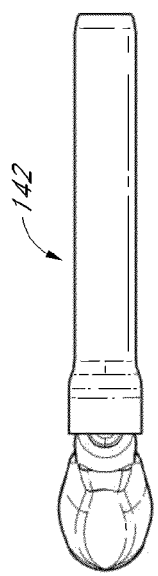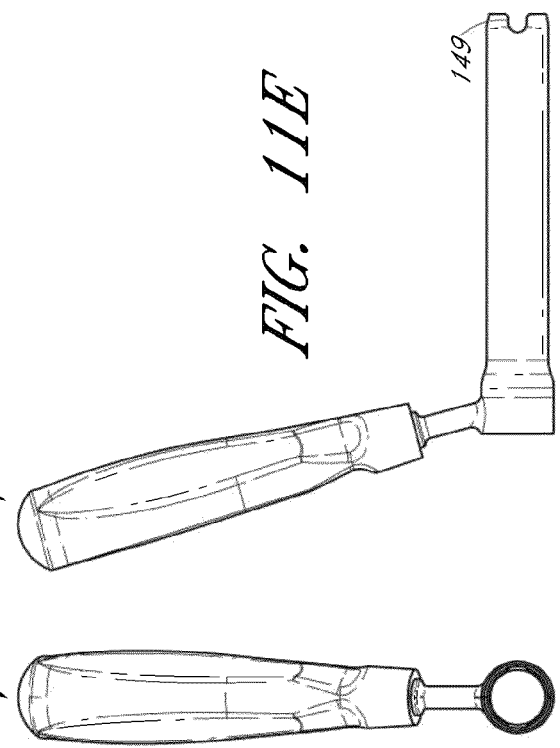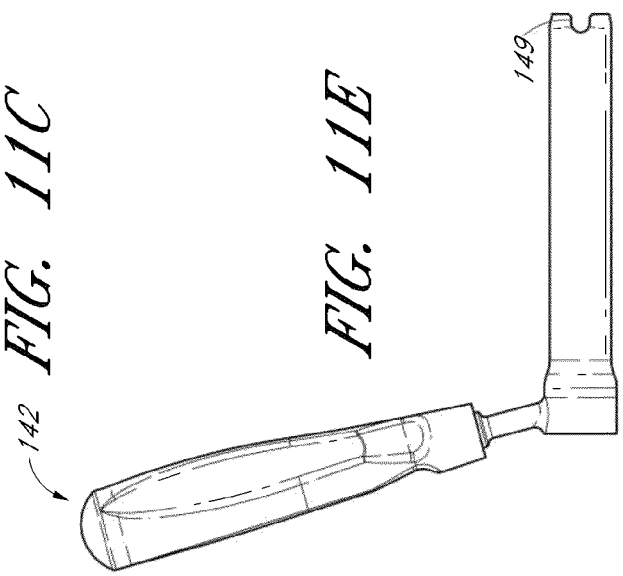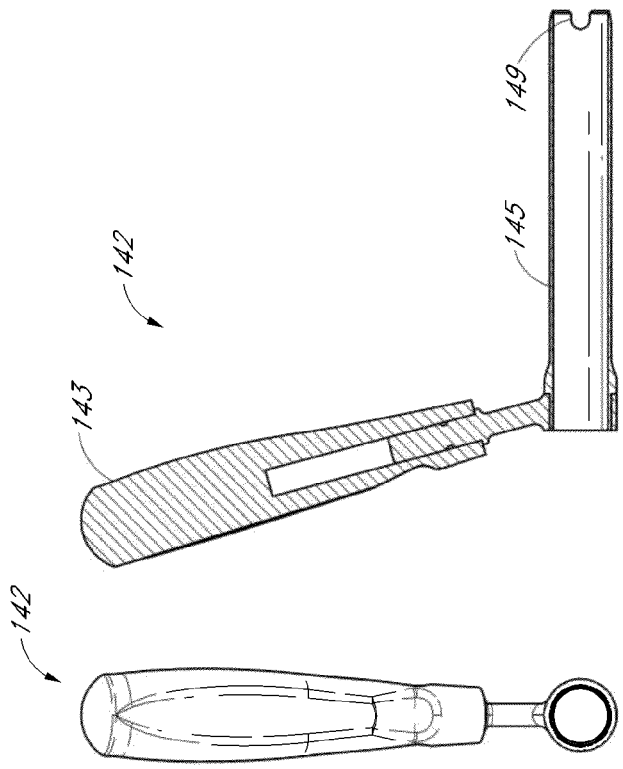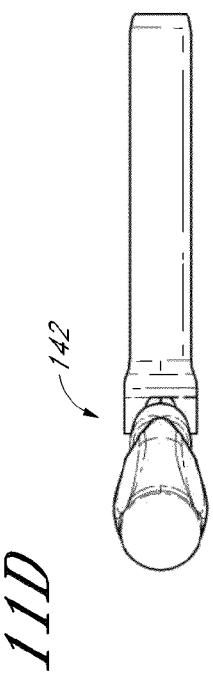

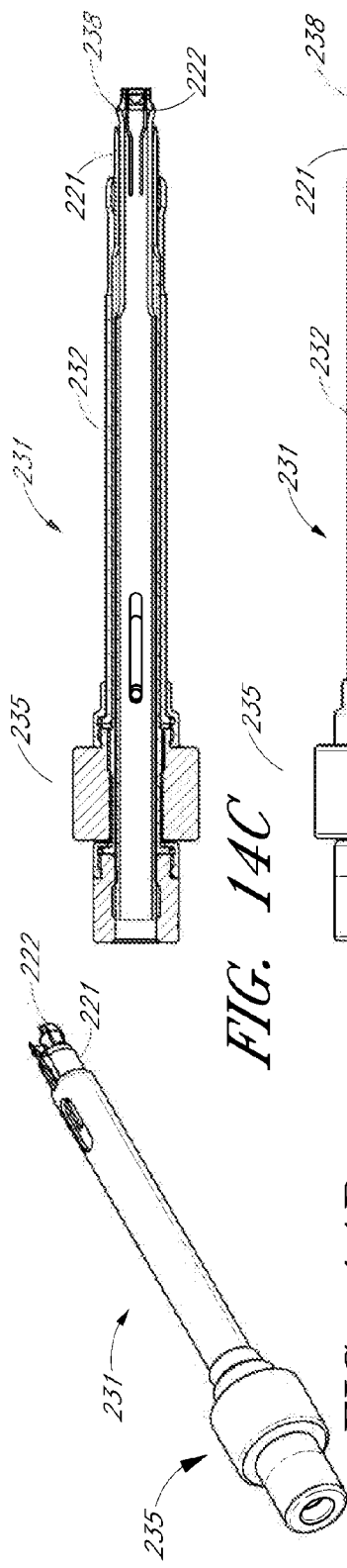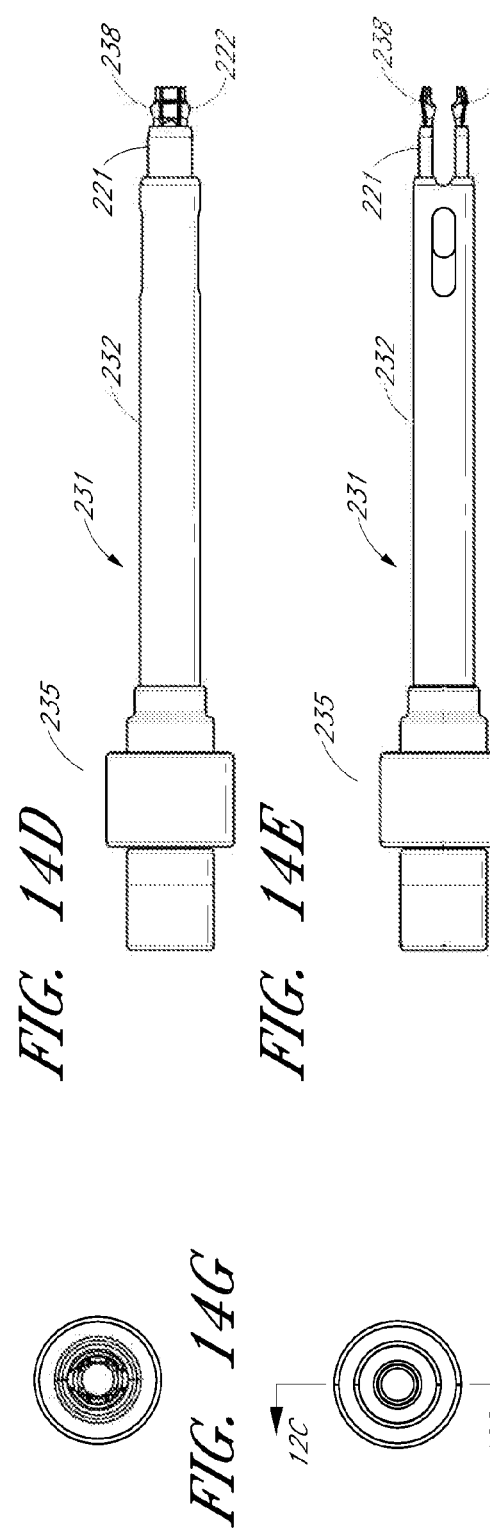
FIG. 14B
FIG. 14C
FIG. 14D
FIG. 14E
FIG. 14F
FIG. 14G
FIG. 14H

MINIMALLY INVASIVE SURGICAL TOWER ACCESS DEVICES AND RELATED METHODS

BACKGROUND OF THE INVENTION

1. Field of the Invention

The present application relates to devices and methods for providing spinal stabilization. In particular, the present application relates to minimally invasive devices and methods for delivering fixation devices and implants into a spine.

2. Description of the Related Art

Spinal bone degeneration can occur due to trauma, disease or aging. Such degeneration can cause abnormal positioning and motion of the vertebrae, which can subject nerves that pass between vertebral bodies to pressure, thereby causing pain and possible nerve damage to a patient. In order to alleviate the pain caused by bone degeneration, it is often helpful to maintain the natural spacing between vertebrae to reduce the pressure applied to nerves that pass between vertebral bodies.

To maintain the natural spacing between vertebrae, spinal stabilization devices are often provided to promote spinal stability. These spinal stabilization devices can include fixation devices, such as spinal screws, which are implanted into vertebral bone. The fixation devices work in conjunction with other implanted members, such as rod members, to form stabilization systems.

Conventional stabilization systems often require open surgeries and other invasive procedures in order to deliver the implants into the body. These invasive procedures often cause a great deal of pain and trauma to the patient, and require a substantial recovery time. Thus, there exists a need for minimally invasive devices and methods that can assist in providing spinal stabilization.

SUMMARY OF SOME EMBODIMENTS

Devices and methods are provided for assisting in spinal stabilization. In some embodiments, a system for spinal stabilization is provided. The system comprises a percutaneous access device including an outer sleeve having a proximal slot and a distal slot. The access device also includes an inner sleeve having a proximal section and a distal section, the proximal section being operably connected to a spring latch having a tab member and including a threaded portion, the distal section including a slot and a pair of compressible grasping elements, each of the grasping elements including slits, an internal tapered surface, and an internal protruding member capable of being received in an aperture in a head of a screw member, wherein the inner sleeve is configured to be slidably received into the outer sleeve such that the spring latch is located within the proximal slot of the outer sleeve and the slot of the inner sleeve is aligned with the distal slot of the outer sleeve. In addition, the access device can include a lock nut having an internal engagement surface for engaging the threaded portion of the inner sleeve, wherein placement of the lock nut at a bottom section of the threaded portion of the inner sleeve results in compression of the grasping elements, and wherein the internal engagement surface is configured to interact with the tab member via depressions to limit counter rotation of the lock nut during use.

The system can also include a cannulated screw member that is attachable to the inner sleeve. The cannulated screw member comprises a head portion coupled to a shaft, wherein the head portion includes a seat for receiving a rod implant, one or more apertures for receiving an internal protruding member of the inner sleeve, and at least one slot for interacting with the internal tapered surface of the inner sleeve. A screw driver for rotating and driving the screw member into bone can also be provided, as well as a rod insertion device including a handle and a distal gripping end for gripping and delivering a rod member.

The system can also include an anti-torque device including a handle connected to a cannula, wherein the cannula is configured to be placed over the outer sleeve, and wherein the cannula includes a side slot for engaging the rod member. A persuader device including internal threads can also be provided that can interact with the anti-torque device and assist in forcing the rod member into the seat of the screw member.

In other embodiments, an alternative spinal stabilization system is provided. The system comprises an outer sleeve having a distal slot. The system also comprises an inner sleeve having a proximal section and a distal section, the proximal section including a threaded portion, the distal section including a slot and a pair of compressible grasping elements, each of the grasping elements including an internal protruding member. The inner sleeve can be configured to be slidably received into the outer sleeve such that the slot of the inner sleeve is aligned with the distal slot of the outer sleeve, and wherein sliding the outer sleeve relative to the inner sleeve actuates compression of the grasping elements of the inner sleeve.

In other embodiments, a method of spinal stabilization is provided. A first access device can be provided that includes a first outer sleeve and a first inner sleeve, wherein the first inner sleeve includes a pair of compressible grasping elements actuated by sliding the first inner sleeve relative to the first outer sleeve. A first screw member can be provided within the first pair of compressible grasping elements. The first pair of compressible grasping elements can be compressed to couple the first access device to the first screw member. The first access device and first screw member can be delivered to a first location within a patient. The first screw member can be inserted into a first bone member of the patient. A second access device can be provided that includes a second outer sleeve and a second inner sleeve, wherein the second inner sleeve includes a pair of compressible grasping elements actuated by sliding the second inner sleeve relative to the second outer sleeve. A second screw member can be provided within the second pair of compressible grasping elements. The second pair of compressible grasping elements can be compressed to couple the second access deice to the second screw member. The second access device and second screw member can be delivered to a second location within a patient. The second screw member can be inserted into a second bone member of the patient. A rod member can be delivered to connect between the first screw member and second screw member.

BRIEF DESCRIPTION OF THE DRAWINGS

FIG. 2 illustrates an exploded view of different components of the tower access device of FIG. 1 according to embodiments of the present application.

FIGS. 3A-3G illustrate several views of an outer sleeve member according to embodiments of the present application.

FIGS. 4A-4G illustrate several views of an inner sleeve member according to embodiments of the present application.

FIGS. 9A and 9B illustrate a rod insertion device according to embodiments of the present application.

FIGS. 11A-11G illustrate different views of an anti-torque device according to embodiments of the present application.

FIGS. 14A-14H illustrate different views a persuader system according to embodiments of the present application.

DETAILED DESCRIPTION OF EMBODIMENTS

The present application relates to minimally invasive devices and methods for assisting in the delivery of fixation devices and other implants in a patient. While the minimally invasive devices described herein can be used to assist various treatments, in some embodiments, they are used to assist in delivering fixation devices and other implants to help stabilize the spine.

In some embodiments, a minimally invasive tower access device is provided. The access device includes an outer sleeve and an inner sleeve that telescopingly or slidably engage with one another. The inner sleeve includes one or more grasping elements that can grasp a fixation device (e.g., a pedicle screw) for delivery into a bone member of a spine. Once the access device is coupled to the spinal screw, the access device and spinal screw can be delivered either through an incision in an open surgery, or minimally invasively through a relatively smaller incision, such as percutaneously. Once through the incision, the spinal screw can be brought to a location proximate to a bone member where it can be inserted. The access device can serve as a portal or opening that extends from the bone member to outside of the patient. Instruments can be delivered through the access device. For example, a screw driver can be provided through the access device to secure the spinal screw to the bone member. In addition, implants can be delivered adjacent the side of the access device. For example, a rod implant can be delivered along the side of the access device which can connect in between the implanted screws. By using one or more access devices to deliver screws or other implants as described herein, a spinal stabilization system can be formed. The one or more access devices advantageously allow screws and other implants to be inserted in a specific location with ease, and allow for a surgeon to comfortably maintain external control of the screw from outside of a patient's body.

A number of additional instruments can be used with the access device to provide spinal stabilization. Among the instruments that can be used include a screw driver, a rod insertion device, an anti-torque device, and a rod persuader device. These instruments, as well as the access device, will be discussed in greater detail below.

Minimally Invasive Tower Access Device

Figure 1:
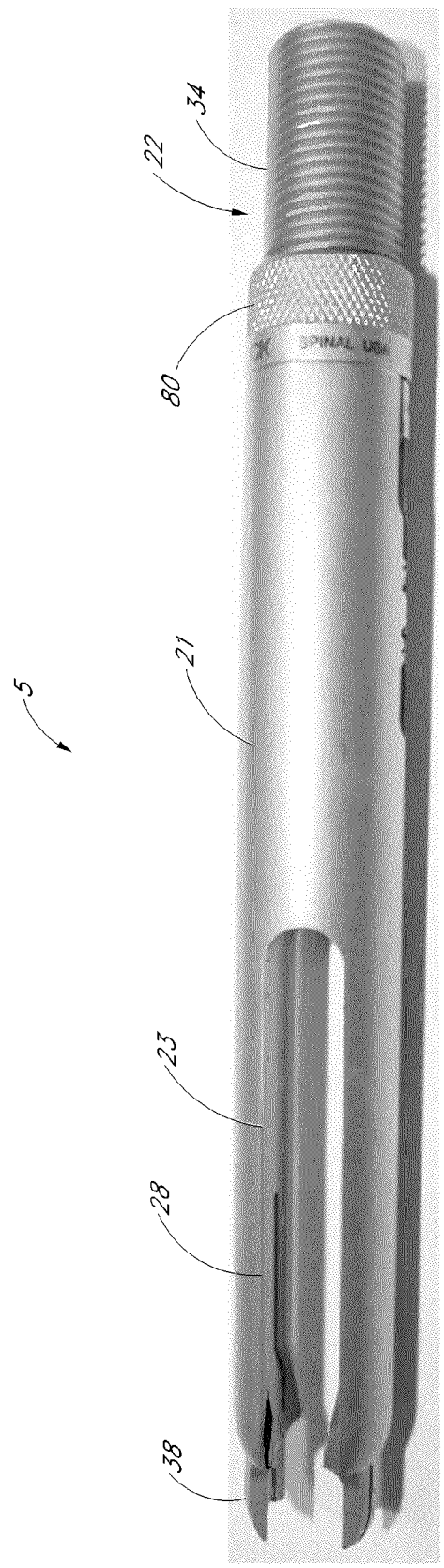
FIG. 1 illustrates a side view of an assembled minimally invasive tower access device according to embodiments of the present application.

FIG. 1 illustrates a side view of an assembled minimally invasive tower access device according to embodiments of the present application. The access device 5 includes an elongated outer sleeve 21 and an elongated inner sleeve 22 that are slidably engaged with each other. The access device 5 also includes a spring latch 60 (shown in FIGS. 2 and 5). A lock nut 80 is also provided that engages with a threaded portion of the inner sleeve 22. When all of the components are assembled as shown in FIG. 1, they form an access device 5 that can couple to a fixation device, such as a screw. The coupled access device and screw can be delivered to a target location of a patient. In some embodiments, the access device and screw member are delivered percutaneously.

FIG. 2 illustrates an exploded view of different components (e.g., the outer sleeve, inner sleeve, and lock nut) of the tower access device of FIG. 1 according to embodiments of the present application. Each of these components will be discussed in greater detail below.

FIGS. 3A-3G illustrate several views of an outer sleeve member 21 according to embodiments of the present application. The outer sleeve 21 includes two slots, a proximal slot 27 and a distal slot 28. In other embodiments, the outer sleeve 21 can have a single distal slot. Within the outer sleeve member 21 is a hollow cylindrical body through which an inner sleeve can be received.

The proximal slot 27 and distal slot 28 are formed on opposite ends of the outer sleeve 21—the proximal slot 27 is formed on a proximal end of the outer sleeve 21 while the distal slot 28 is formed on a distal end of the outer sleeve 21. As used herein, the term "proximal end" refers to the end of the access device that is closer to the end exposed during surgery, while the term "distal end" refers to the end of the access device that is closer to a target location within a patient for delivering a fixation device or implant. While both the proximal slot 27 and the distal slot 28 are formed along an edge of the outer sleeve 21, in some embodiments, either one or both slots can be formed within the body of the outer sleeve 21 instead of along an edge.

In some embodiments, the proximal slot 27 opens along one side of the outer sleeve 21, while the distal slot 28 opens along two sides of the outer sleeve 21 (as shown in FIG. 3A). The proximal slot 27 can be located in between the two openings that form the distal slot 28. While a center longitudinal axis of the proximal slot 27 is shown at about a 90 degree angle from the a center longitudinal axis of the distal slot 28, the proximal slot 27 can be located at any angle relative to the openings of the distal slot 28, such as between 0 and 90 degrees. While the proximal slot 27 is smaller in both width and length than the distal slot 28 in the illustrated embodiment, the two slots need not be limited to these relative dimensions.

Both the proximal slot 27 and the distal slot 28 of the outer sleeve 21 can serve particular functions. In some embodiments, the proximal slot 27 can serve to receive the spring latch 60, which can be fixed to the inner sleeve 22. The proximal slot 27 can work in conjunction with the spring latch 60 to identify the current mode of operation of the access device 5 (e.g., "locked" or "unlocked" mode) as best shown in FIG. 8E. The spring latch 60 can include a marker 69 (shown in FIG. 8E) that can help identify the particular mode of operation. The different modes of operation will be discussed below. With the spring latch 60, the mode of operation of the access device will be easily visible to the surgeon. In addition, having the proximal slot 27 work in conjunction with the spring latch 60 advantageously allows for proper placement of the outer sleeve 21 relative to the inner sleeve 22, such that they can have aligning distal slots when the spring latch 60 is inserted in the proximal slot 27 of the outer sleeve.

In some embodiments, the distal slot 28 can serve to receive one or more stabilization implants therethrough. For example, in some embodiments, a stabilizing rod member can be delivered along the side of the access device 5 and angled through the distal slot 28. Once the rod member is angled through the distal slot 28, it can be forced downward onto the head of the screw. Then, one end of the rod member can be fixed to a first screw, while the second end of the rod member is fixed to a second screw, thereby providing spinal stabilization.

The distal slot 28 of the outer sleeve 21 can have a length between 4 cm and 8 cm, or a length between 6 cm and 7 cm. In some embodiments, the length of the distal slot 28 is much longer (e.g., at least 5.5 cm) than slots in conventional access devices. In some embodiments, the length of the distal slot 28 of the outer sleeve 21 is between ⅓ and ¾, or approximately ½ in some instances, the length of the entire body of the outer sleeve. In some embodiments, as shown in FIGS. 8H'-8J', the distal slot 28 of the outer sleeve can be even longer, and can extend almost the entire length of the outer sleeve 21. The advantage of the longer slot is that a rod implant can be more easily delivered through the slot to provide spinal stabilization. In addition, providing a longer slot length makes the instrument lighter by removing material from the system. A challenge, however, is that with the longer slot, the sidewalls that form the slot may need to be stronger in order to withstand forces on the sidewalls in some embodiments. Accordingly, in some embodiments, the thickness of the sidewalls that form the longer distal slot 28 of the outer sleeve 21 is preferably increased relative to conventional sleeves to withstand forces on the sidewalls. In some embodiments, the thickness of the sidewalls that form the longer distal slot 28 is between about 0.05 cm and 0.4 cm, or between about 0.2 cm and 0.3 cm.

FIGS. 4A-4G illustrate several views of an inner sleeve member 22 according to embodiments of the present application. The inner sleeve 21 includes a proximal section 31 and a distal section 33. The distal section 33 includes a distal slot 23 and a pair of grasping elements 38. The inner sleeve 22 can be slidably received within the outer sleeve 21, and in some embodiments, can be secured in a position relative to the outer sleeve 21 by using the lock nut 80. Like the outer sleeve 21, the inner sleeve 22 includes a hollow cylindrical body. In some embodiments, the inner sleeve has an interior diameter of between about 0.5 cm and 2 cm, or between about 1.0 cm and 1.1 cm.

In some embodiments, the proximal section 31 of the inner sleeve 22 includes an exposed threaded portion 34, as shown in FIG. 1. A lock nut 80 having internal threads can engage with the exposed threaded portion 34 of the inner sleeve. By rotating the lock nut 80 in a clockwise direction until it is at a bottom section of the exposed threaded portion 34, the outer sleeve 21 can be secured with the inner sleeve 22 in a "locked" mode in which the compressible grasping elements 38 of the inner sleeve 21 are compressed (discussed below).

Below the proximal section 31 of the inner sleeve 22 is the distal section 33 including a distal slot 23 and compressible grasping elements 38. Like the distal slot 28 of the outer sleeve 21, the distal slot 23 of the inner sleeve 22 can open on two sides of the inner sleeve 22. In some embodiments, the distal slot 23 of the inner sleeve 22 is approximately the same size (e.g., similar width and height) of the distal slot 28 of the outer sleeve 21. One skilled in the art will appreciate that the dimensions of both the distal slot 28 of the outer sleeve 21 and slot 23 of the inner sleeve 22 can vary with respect to one another. The distal slot 23 of the inner sleeve 22 can be placed in part or in complete alignment with the distal slot 28 of the outer sleeve 21. In some embodiments, when the distal slot 23 of the inner sleeve 22 is aligned with the distal slot 28 of the outer sleeve 21, a rod implant that is delivered into the patient can pass through both of the slots. The rod implant can be angled through the slots such that each end of the rod implant makes contact with a screw head within the access device.

The distal slot 23 of the inner sleeve 22 can have a length between about 4.0 cm and 8.0 cm, or between about 6.0 cm and 7.0 cm. In some embodiments, the length of the distal slot 23 is much longer (e.g., at least 5.5 cm) than slots in conventional access devices. In some embodiments, the length of the distal slot 23 of the inner sleeve 22 is between ⅓ and ¾, or approximately ½ in some instances, the length of a nonthreaded body of the inner sleeve 22.

Figure 4A:
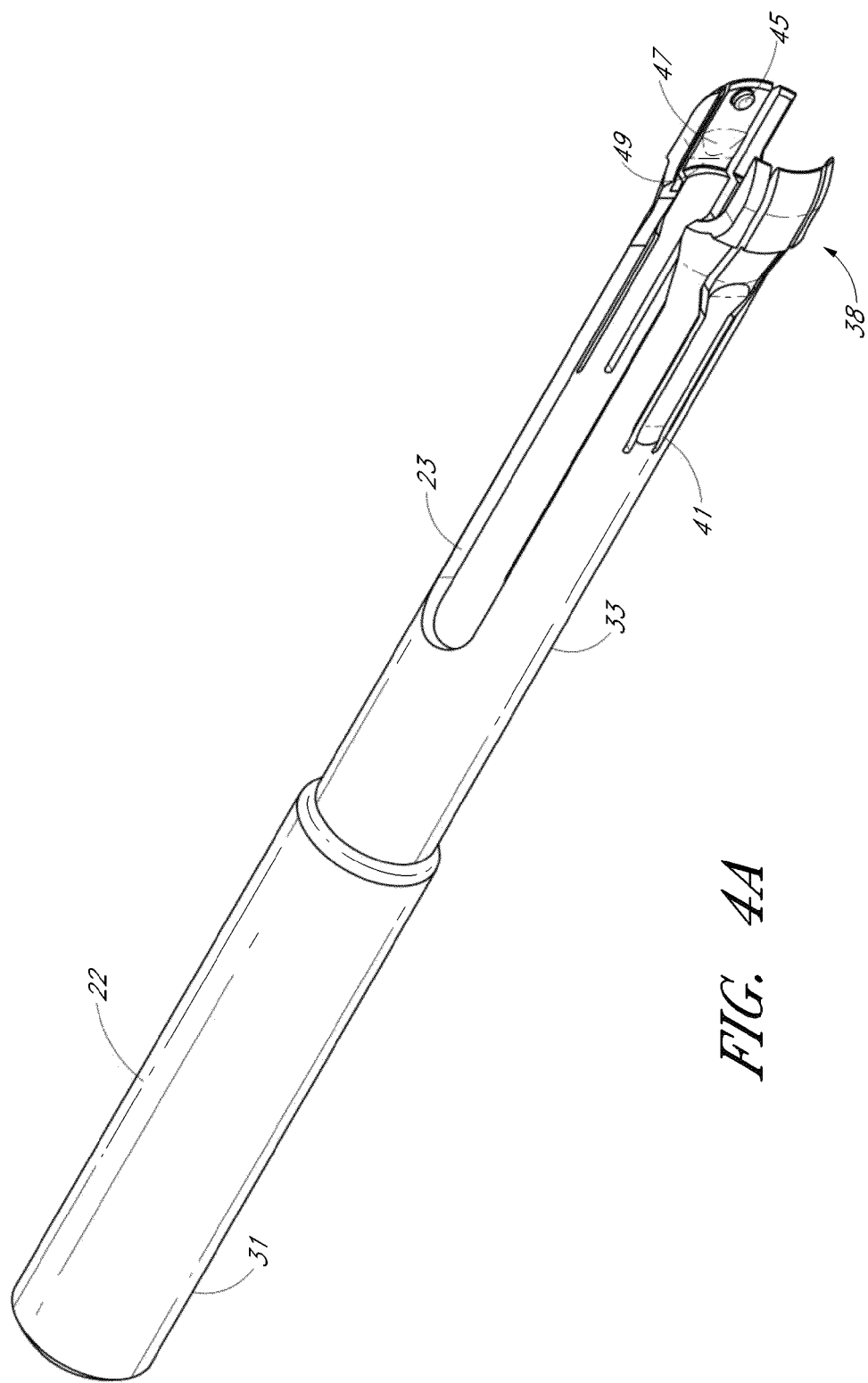
Figure 5A:
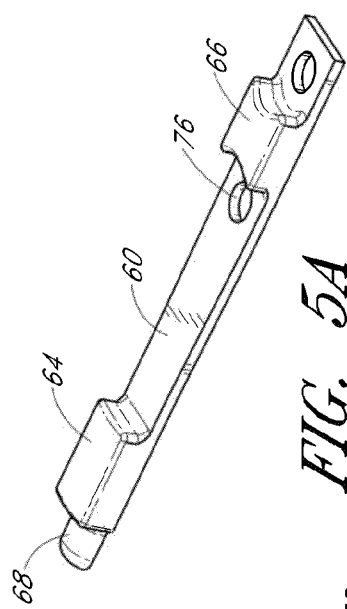
FIGS. 5A-5G illustrate several views of a spring latch member according to embodiments of the present application.
Figure 5F:
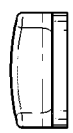
Figure 5G:
Figure 5B:
Figure 5C:
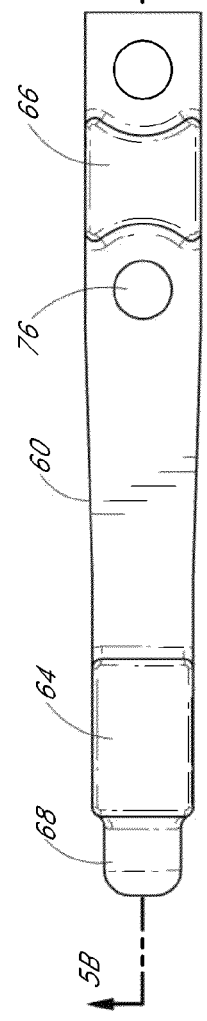
Figure 5D:
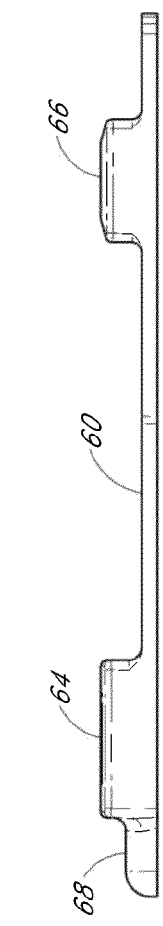
Figure 5E:
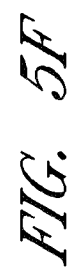

In some embodiments, the pair of grasping elements 38 comprise a pair of compressible arms or tines for receiving a screw head, as shown in FIG. 4A. One skilled in the art will appreciate that the shape of the grasping elements 38 need not be limited to the description described herein. In some embodiments, the distance from one grasping element to another is slightly greater than the diameter of the hollow interior of the outer sleeve 21 in an uncompressed state. In these embodiments, in order for the inner sleeve 22 to be received through the proximal end of the outer sleeve 21, the grasping elements 38 should be slightly compressed. When the grasping elements 38 exit the distal end of the outer sleeve 21, the grasping elements 38 can return to their uncompressed state, thereby advantageously helping to secure the inner sleeve 22 to the outer sleeve 21 by limiting the inner sleeve 22 from unintentionally backing out of the outer sleeve 21.

In some embodiments, the grasping elements 38 are flat, while in other embodiments (as shown in FIG. 4A), the grasping elements 38 can include some curvature so as to accommodate a screw head of a particular shape. In some embodiments, the grasping elements 38 include protruding members 45 that can be received in an aperture of the screw head to secure the screw to the inner sleeve. The protruding members 45 can be rigid or somewhat flexible, and are configured to be inserted into two or more holes or apertures formed on the head of a screw upon compression of the grasping elements 38 of the inner sleeve 22. While the protruding members 45 can have a smooth surface finish, in some embodiments, the protruding members 45 have a roughened surface finish that can provide a frictional force between the protruding members 45 and surfaces of the screw head that form the receiving apertures 45. The protruding members 45 can have a cross-sectional area that is circular, rectangular, trapezoidal or any other shape, so long as they are securely receivable in a corresponding aperture of the head of the screw. In some embodiments, rather than have protruding members that resemble pins, the inner sleeve 22 can include flanges that extend from a bottom surface of the distal end of the inner sleeve 22. The flanges can be compressible such that when compressed, the flanges surround and secure a portion of the head of the screw (such as a bottom portion), thereby coupling the inner sleeve 22 to the screw.

In some embodiments, the compressible grasping elements 38 of the inner sleeve 22 also include an internal surface 47 (shown in FIG. 4A) for engaging a slot on the screw head. The purpose of the internal surface 47 is to absorb axial force that is transferred to the grasping elements 38 of the inner sleeve 22 from the screw head when the screw head is under compression. The internal surface 47 can engage one or more slots located on the screw head, and can comprise a substantially triangular tapered surface proximal from the protruding member 45. In some embodiments, the substantially triangular tapered surface 47 can be located below a ledge 49 that forms an indentation in the interior of the grasping elements 38. The ledge 49 can advantageously provide a surface for the screw to stop against once the screw is inserted to its proper depth within the inner sleeve 22.

In some embodiments, the grasping elements 38 include optional slits 41, which advantageously assist to provide compressibility to the grasping elements 38. The compressibility of the grasping elements 38 is advantageous as it allows the inner sleeve to be received in the outer sleeve, and also helps the grasping elements 38 to couple with a screw head. As shown in FIG. 4A, in some embodiments, each of the grasping elements 38 can include a pair of slits 41 such that each grasping element is divided into three sections—two side sections and a middle section. In these embodiments, the middle section can include a protruding member 45 and internal tapered surface 47, as discussed above.

The inner sleeve 22 can be slidably received in the outer sleeve 21 such that the grasping elements 38 of the inner sleeve 22 can extend beyond the distal end of the outer sleeve 21. In some embodiments, the inner sleeve 22 can be slidably received in the outer sleeve 21 such that in a first position, the grasping elements 38 are uncompressed. Sliding the inner sleeve 22 relative to the outer sleeve 21 in a second position can result in compression of the grasping elements 38. For example, the outer sleeve 21 can be slid down the inner sleeve 22 such that a bottom of the outer sleeve 21 helps to compress the grasping elements 38. In some embodiments, the outer sleeve 21 can completely cover the grasping elements 38 to compress the grasping elements, while in other embodiments, the outer sleeve 21 only covers a portion of the grasping elements 38 to result in compression. The compression mechanism provided by the outer sleeve 21 sliding over the compressible grasping elements 38 of the inner sleeve 21 is advantageous over conventional screw delivery devices, as the body of the outer sleeve 21 helps to reduce the risk of the protruding members 45 becoming accidentally loose from the head of the screw. Moreover, having a slidably engaged outer sleeve 21 and inner sleeve 22 reduces the need for extra tools that might be used in conventional screw delivery devices for securing an access device to a screw member. In some embodiments, the inner sleeve 22 and outer sleeve 21 can work in conjunction with a lock nut 80 to secure the inner sleeve 22 and outer sleeve 21 in a position such that the grasping elements are compressed. The inner sleeve 22 and outer sleeve 21 can also work in conjunction with a spring latch 60.

FIGS. 5A-5G illustrate several views of a spring latch member 60 according to embodiments of the present application. The spring latch 60 includes an upper raised surface 64 and a lower raised surface 66, as well as a tab member 68 extending from a proximal end. The spring latch 60 can also include holes 76 for receiving one or more fixation members (e.g., screws) for attaching the spring latch 60 to the inner sleeve 22.

In some embodiments, and as shown in FIG. 8E, the spring latch 60 can be attached to the inner sleeve 22. The spring latch 60 can serve multiple functions. In some embodiments, the spring latch 60 (when fixed to the inner sleeve 22) can fit within the proximal slot 27 of the outer sleeve 21 and can serve to identify the current mode of operation of the access device 5 when the inner sleeve 22 and outer sleeve 21 are slid relative to one another. For example, the spring latch 60 can include a marker that can identify when the outer sleeve and inner sleeve are in an "unlocked" position in which the two sleeves remain slidable relative to one another. Or the spring latch 60 can identify when the outer sleeve and inner sleeve are in a "locked" position in which the two sleeves are secured in a position with the lock nut 80. In addition, the spring latch 60 can advantageously help to ensure that the inner sleeve 22 and outer sleeve 21 are in proper alignment, by having the spring latch 60 fit within the proximal slot 27 of the outer sleeve 21.

Figure 6A:
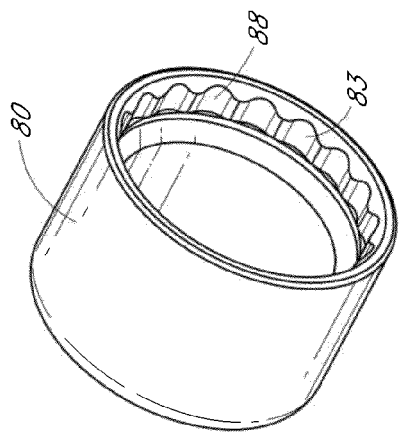
FIGS. 6A-6E illustrate several views of a lock nut according to embodiments of the present application.
Figure 6C:
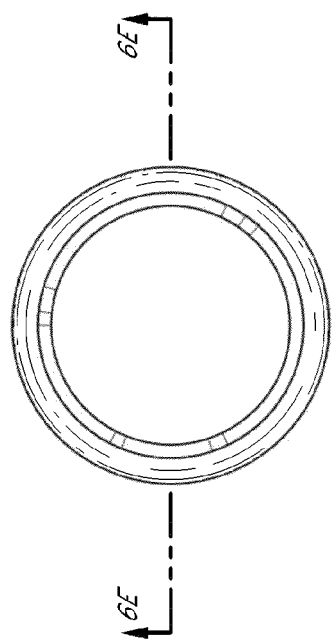
Figure 6B:
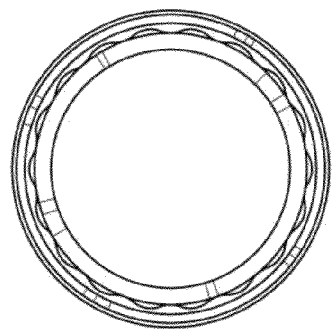
Figure 6E:
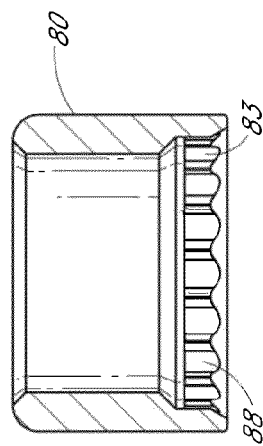
Figure 6D:
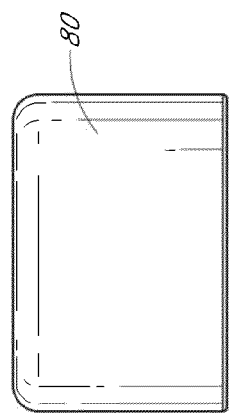
Figure 7A:
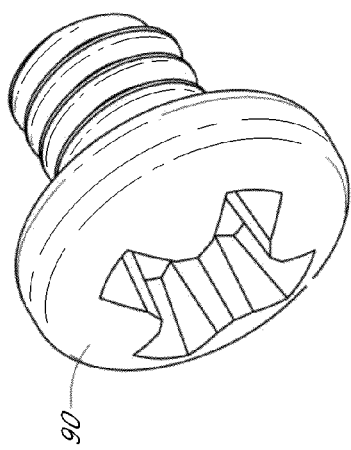
FIGS. 7A-7D illustrate several views of a screw member for using with a spring latch according to embodiments of the present application.
Figure 7B:
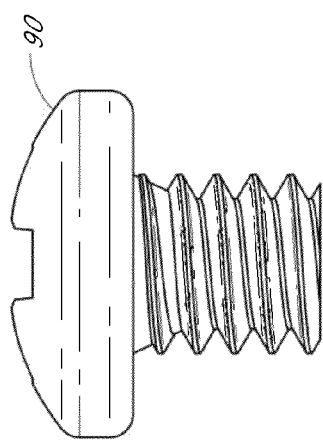
Figure 7C:
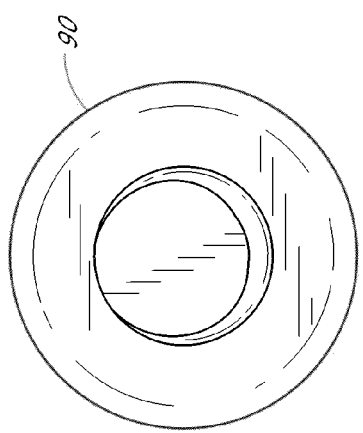
Figure 7D:
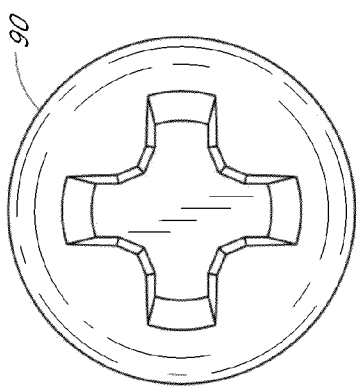

In some embodiments, the tab member 68 of the spring latch can interact with lock nut 80 when the lock nut 80 is rotated to a distal section of the external threaded portion 34 of the inner sleeve. For example, the tab member 68 can interact with an inner engagement surface 83 (e.g., one or more depressions 88 as shown in FIG. 6B) of the lock nut 80. By fitting in one of the depressions 88, the tab member 68 can advantageously limit unintentional counter or back rotation of the lock nut 80 when in use.

FIGS. 6A-6E illustrate several views of a lock nut 80 according to embodiments of the present application. The lock nut 80 includes an inner engagement surface 83 that can engage the external threaded portion of the inner sleeve 22. In some embodiments, the inner engagement surface 83 comprises a threaded portion (not shown) that complements the external threads of the inner sleeve 22. In some embodiments, the inner engagement surface 83 can also include a series of depressions 88 for interacting with the tab member 68 of the spring latch 60. When the lock nut 80 is placed in a downward section of the threaded portion of the inner sleeve 22 fixed to a spring latch 60, a tab member 68 of the spring latch can interact and fit into one of the depressions 88, thereby advantageously limiting unintentional back or counter-clockwise rotation of the lock nut 80. On the exterior of the lock nut 80, a knurled surface is advantageously provided for easy grasping during use.

The lock nut 80 can be used to secure the inner sleeve 22 and outer sleeve 21 in a locked mode by adjusting the lock nut 80 in a clockwise direction down the threaded portion of the inner sleeve 22 until it can no longer turn clockwise. In the locked mode, the inner sleeve 22 is secured in position with the outer sleeve 21, and the grasping elements 38 of the inner sleeve are compressed (as shown in FIG. 8G). In this mode, a screw head or other fixation device can be grasped and secured by the compressed grasping elements 38.

FIGS. 7A-7D illustrate several views of a screw member 90 for use with a spring latch according to embodiments of the present application. The screw member 90 can be inserted into the holes 76 of the spring latch 60 to secure the spring latch 60 to the inner sleeve 22, as shown in FIG. 8E.

FIGS. 8A-8G illustrate a procedure for assembling and operating a tower device according to embodiments of the present application.

Figure 8A:
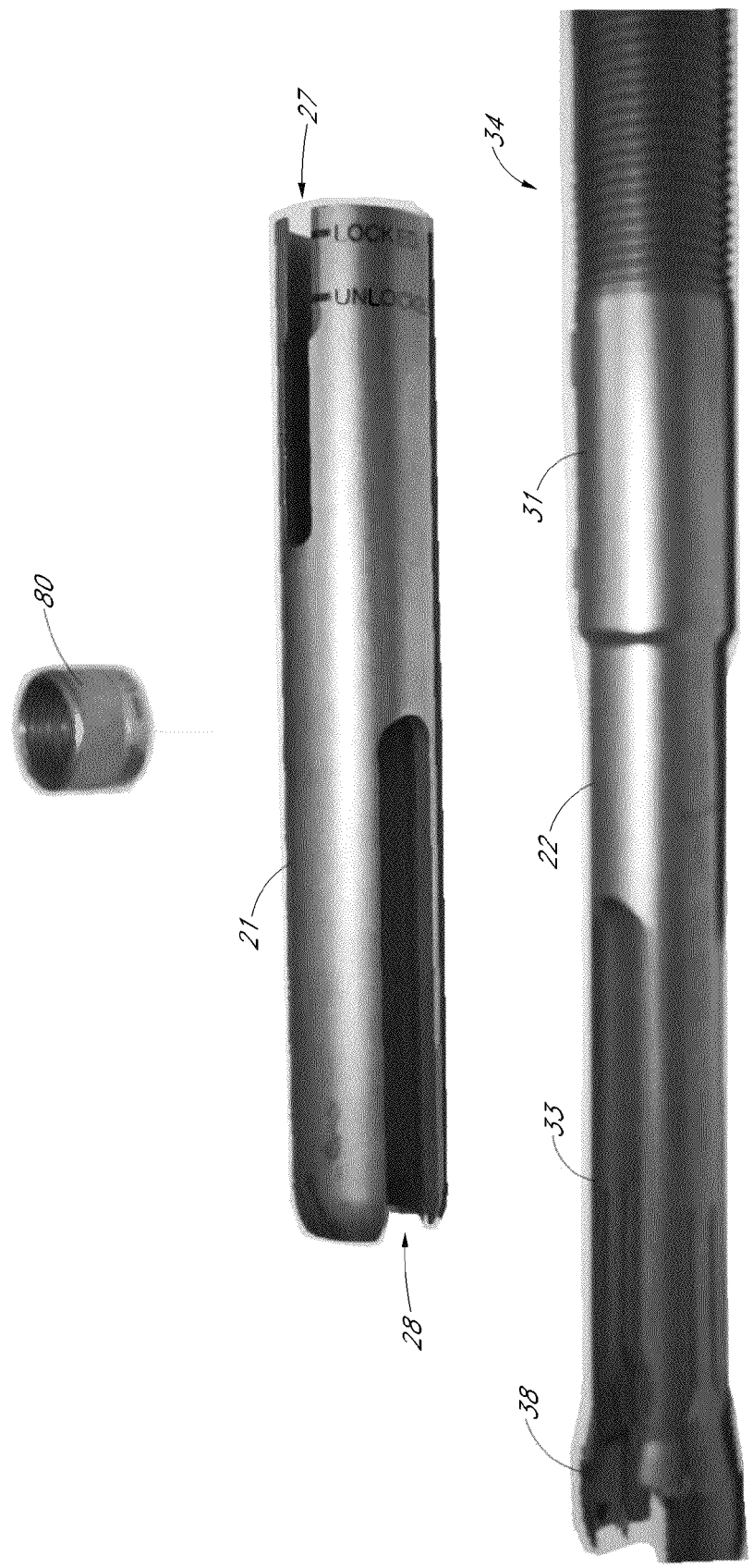
FIGS. 8A-8G illustrate a procedure for assembling and operating a tower device according to embodiments of the present application.

FIG. 8A illustrates the inner sleeve 22, outer sleeve 21 and lock nut 80 as separate components.

Figure 8B:
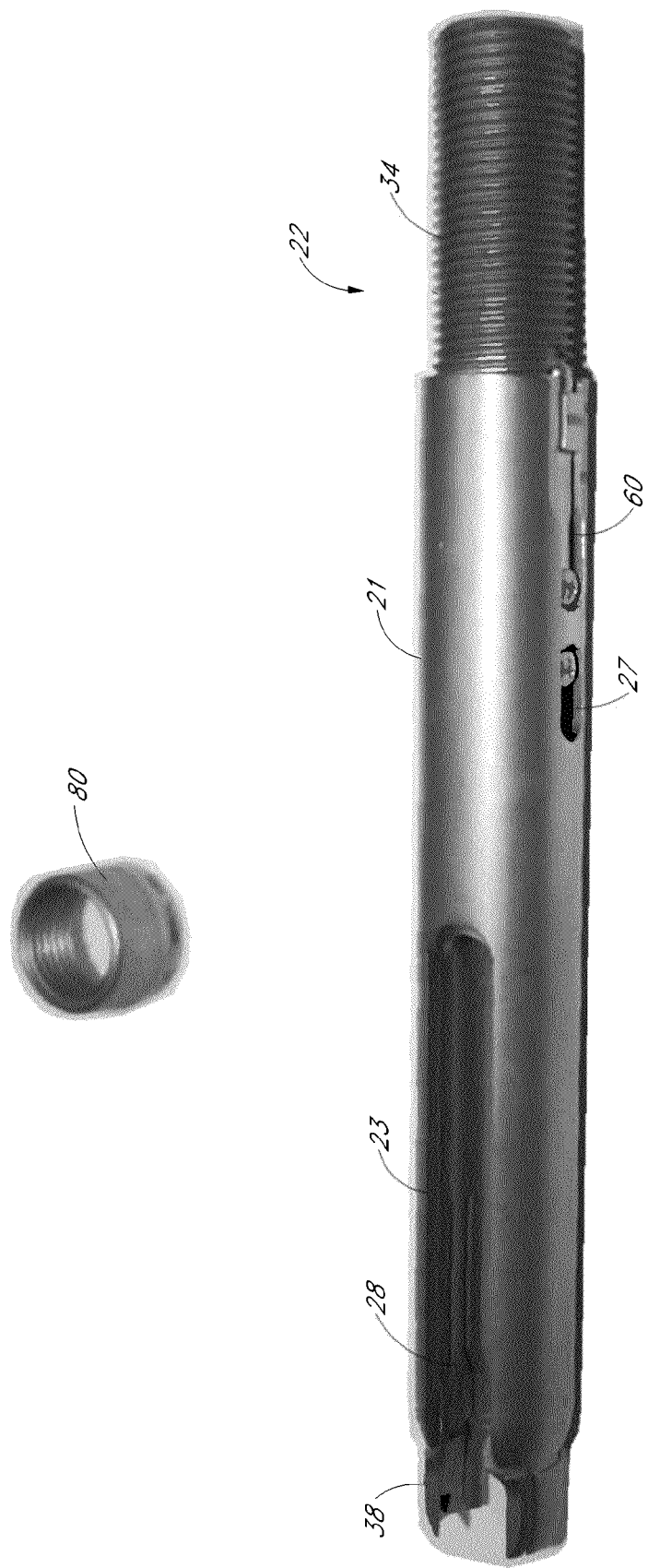
Figure 8C:
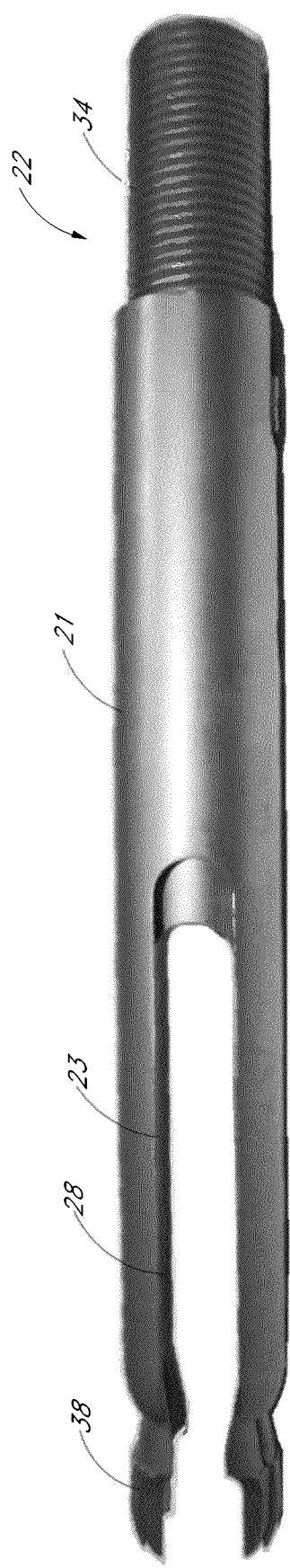

FIGS. 8B and 8C illustrate the inner sleeve 22 inserted into the outer sleeve 21. The inner sleeve 22 is slidable relative to the outer sleeve 21 such that the distal, compressible grasping elements 38 of the inner sleeve extend from a distal end of the outer sleeve 21. In addition, in order to properly orient the inner sleeve 22 relative to the outer sleeve 21, the spring latch 60 (fixed to the inner sleeve) can be aligned with the proximal slot 27 of the outer sleeve 21. In some embodiments, the inner sleeve 22 and outer sleeve 21 are slidable relative to one another until the lock nut 80 is secured in place.

Figure 8D:
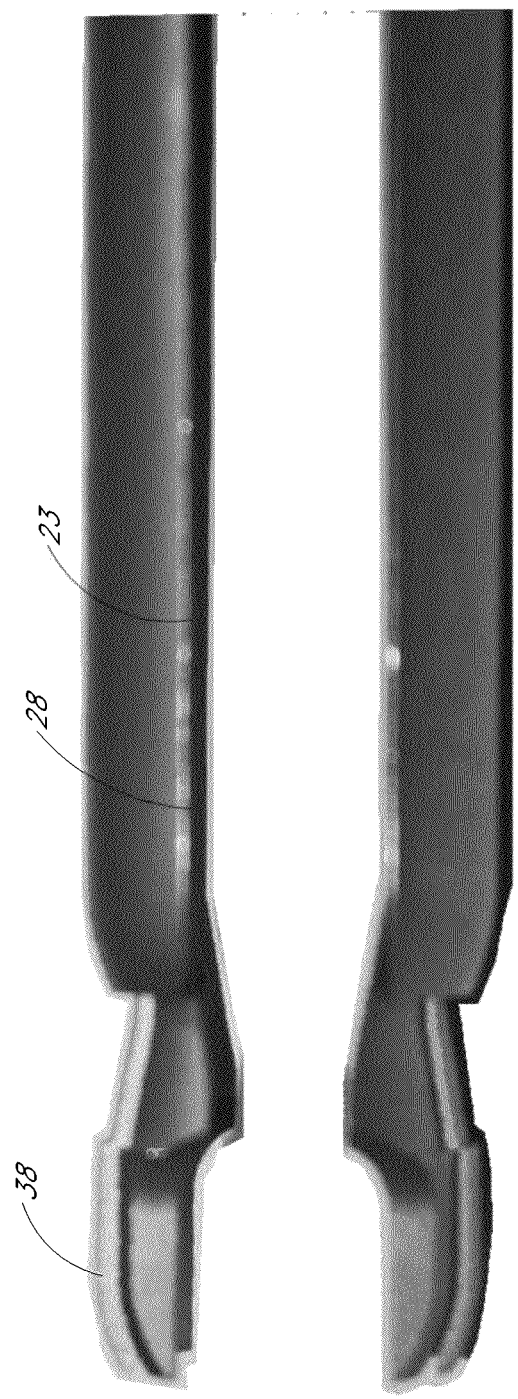
Figure 8E:
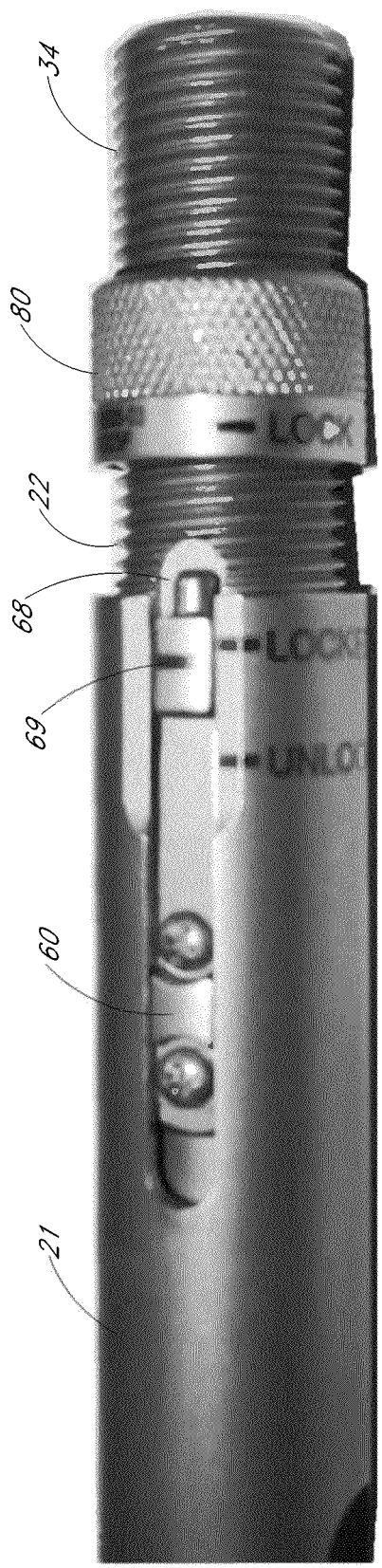

FIG. 8D illustrates a close-up view of the grasping elements 38 upon insertion of the inner sleeve 22 in the outer sleeve 21 without the lock nut 80. The inner sleeve 22 can be moved relative to the outer sleeve 21 such that the grasping elements 38 are open and in an uncompressed state, as shown in FIG. 8D. In the uncompressed state, the grasping elements 38 can easily fit over an object, such as a screw head. The grasping elements 38 can subsequently be compressed (as shown in FIG. 8G) to grasp a screw member with the assistance of the lock nut 80.

FIG. 8E illustrates a close-up view of the lock nut 80 in the process of moving down the threaded portion 34 of the inner sleeve 22. In some embodiments, the lock nut 80 can be rotated clockwise until it is pressed firmly against the surface of the outer sleeve 21. When the lock nut 80 is no longer able to rotate clockwise down the threaded portion 34, the access device 5 will be in locked mode, as indicated by the marker 69 on the spring latch 60. In locked mode, the inner sleeve 22 is secured in a position relative to the outer sleeve 21, and the grasping elements 38 are compressed. In addition, in this mode, the tab member 68 of the spring latch 60 engages an inner portion of the lock nut 80 and limits counter-rotation of the lock nut. Compression of the grasping elements 38 helps to secure the access device to a screw member (e.g., via apertures in the screw head that receive internal protruding members of the grasping elements).

Figure 8F:
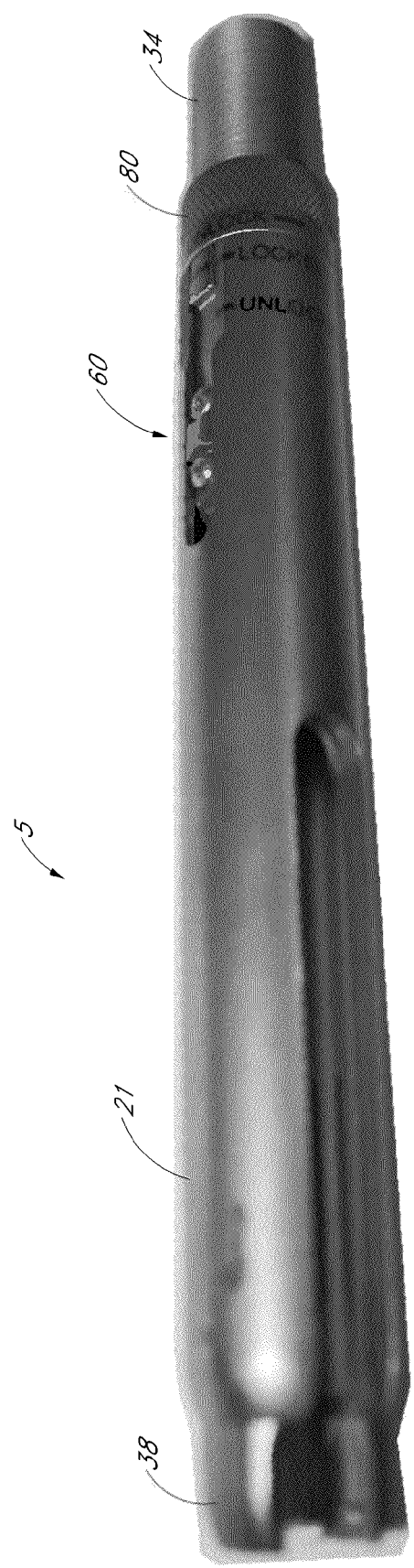
Figure 8G:
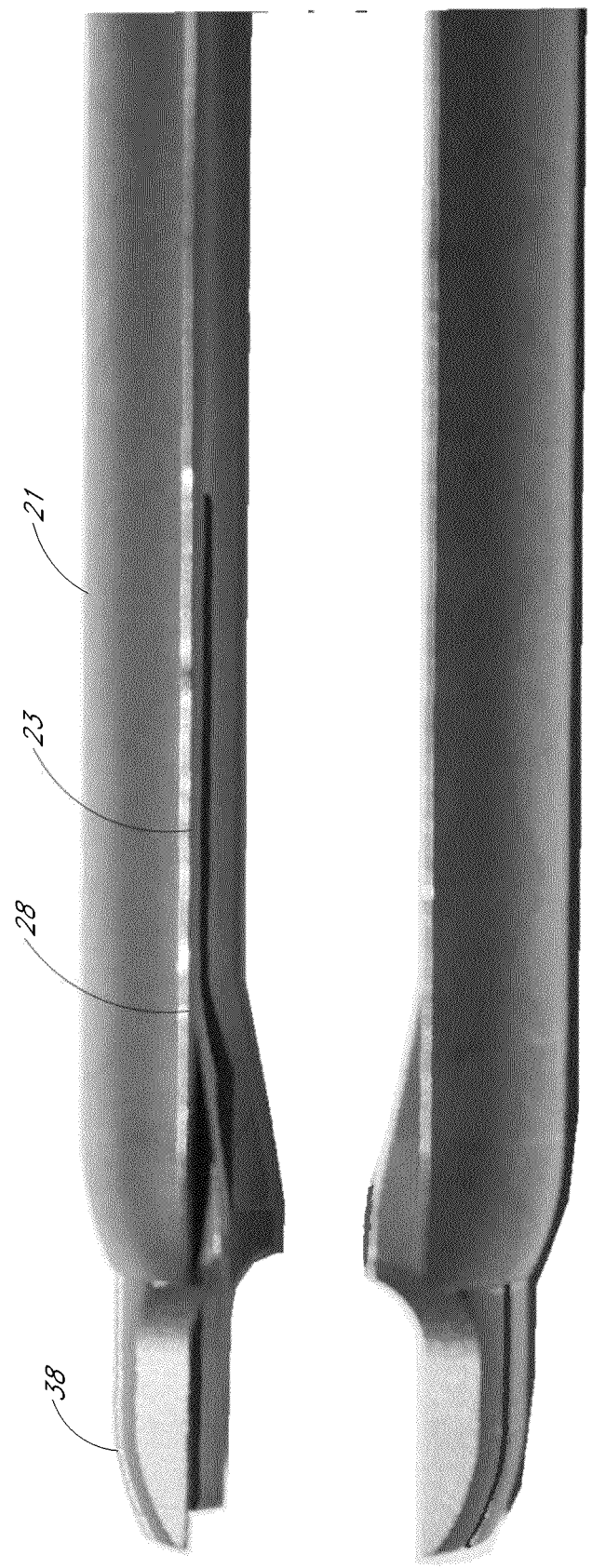

FIG. 8F illustrates a side view of the fully-assembled access device 5 in locked mode. As shown in the figure, the lock nut 80 has been rotated completely clockwise down the threaded portion 34 of the inner sleeve. The tab member 68 of the spring latch is now hidden from view, as it is engaged with an inner portion of the lock nut 80. In the locked mode, the grasping elements 38 are compressed (as shown in FIG. 8G) and capable of securing a screw head therein.

Figure 10A:
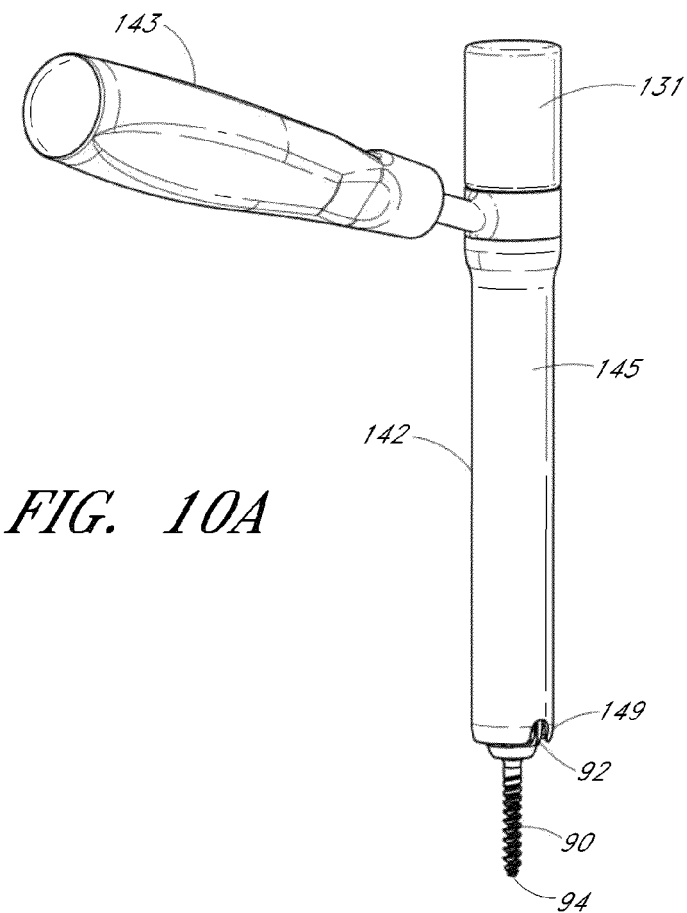
FIGS. 10A and 10B illustrate a rod persuader device and anti-torque device in use according to embodiments of the present application.
Figure 10B:
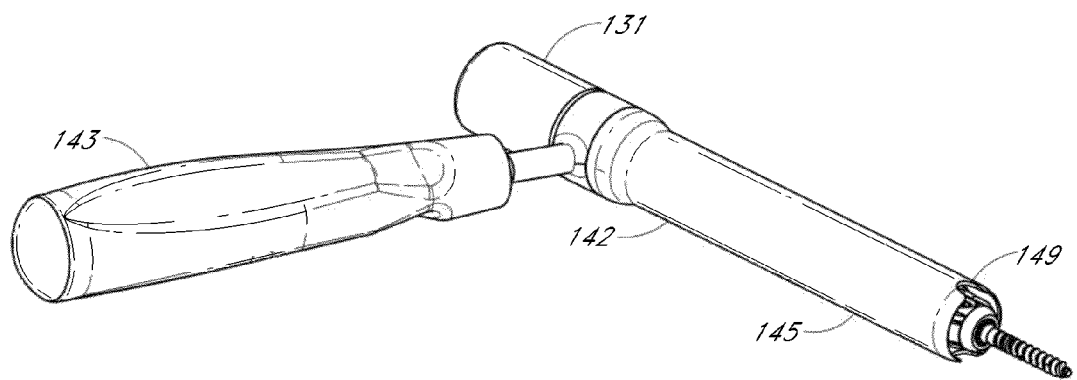
Figure 11A:
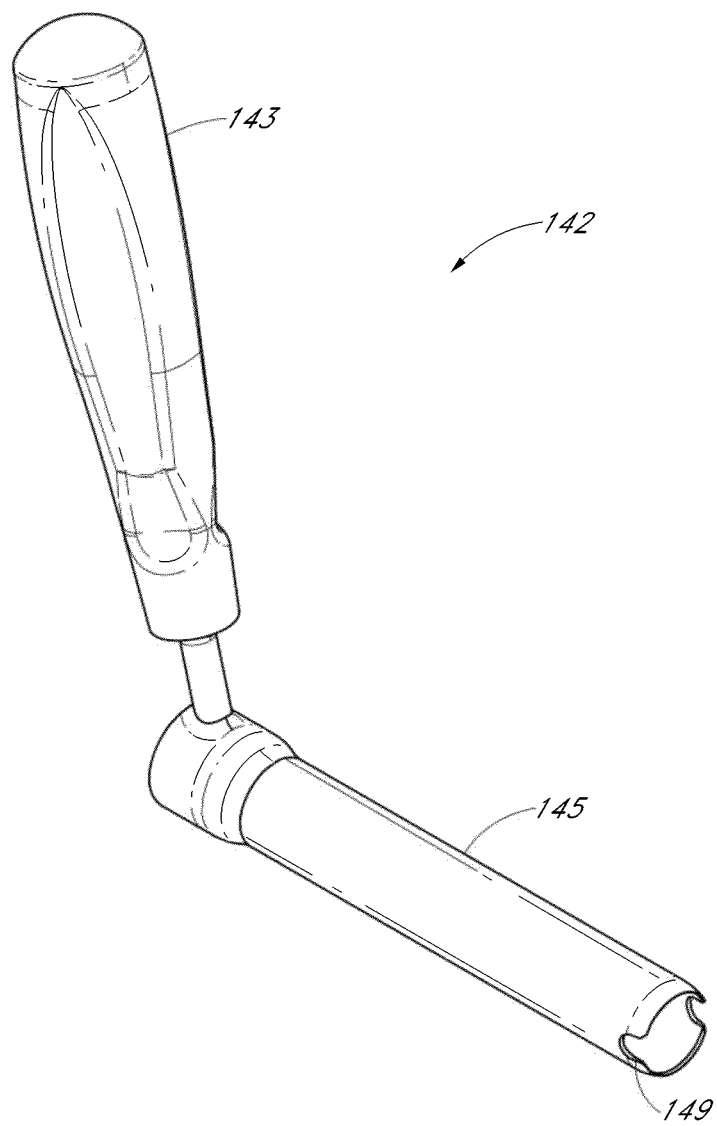

The access device 5 can be coupled to a screw 90 having a head member 92 and threaded shaft portion 94, as shown in FIGS. 10A and 10B. In some embodiments, the head member 92 can be tulip-shaped. The head member 92 can have a U-shaped seat for receiving an implant, such as a stabilizing rod member. The head member 92 can include holes or apertures for receiving one or more protruding members (e.g., from the distal end of the access device). In some embodiments, the surface of the head member 92 also includes one or more slots that interact with the internal tapered surface 47 of the inner sleeve to assist in the absorption of axial loads.

An elongated, threaded shaft member 94 can extend from the bottom of the head member 92. In some embodiments, the head member 92 and shaft member 94 are separate components that are coupled, while in other embodiments, the head member 92 and shaft member 94 form a single unitary member. In some embodiments, the head member 92 of the screw 90 can comprise a break-away portion that is easily separated from the shaft member 94 by a snapping motion. The screw 90 can be cannulated such that it can include a hollow body through which a guidewire or k-wire can be received, as discussed below. Various types of screws can be used with the access device, including different kinds of pedicle screws.

In some embodiments, once the access device 5 and screw 90 are coupled, a screw driver (not shown) can be inserted into the access device. The screw driver, which includes a handle and a shaft, can engage the head of the screw 90 (e.g., a hex portion of the screw). The screw driver can be cannulated such that it too can receive a guidewire or k-wire that passes through the cannulated screw.

The coupled access device 5 and screw 90 (along with the screw driver) can be inserted percutaneously to a target location within the patient (e.g., a portion of a spine) wherein the screw is to be delivered. The coupled access device 5 and screw 90 can be guided using a guide-wire or k-wire that is insertable through the hollow body of the screw 90. Once the screw 90 is placed proximal to a target location, the screw 90 can be driven into the location by using the screw driver to provide rotational and axial force. In some embodiments, rotation of the screw driver causes rotation of the screw 90, as well as rotation of the access device 5 to which it is coupled.

One or more screws can be fixed into bone using the devices described above. For example, in one embodiment, a first screw attached to a first access device can be delivered into a first vertebrae, while a second screw attached to a second access device can be delivered into a second vertebrae. Once the screws are fixed into bone, an implant, such as a connecting rod member (not shown), can be delivered in the patient and connected between the two screws. In some embodiments, the rod member is delivered via a mini-open procedure, in which an incision is made between the first and second screw. In other embodiments, the rod member is delivered percutaneously along the side of either the first and second access devices. One end of the rod member can be fixed to the first screw, while the opposite end of the rod member can be fixed to the second screw, thereby forming a stabilizing connection between the screws. To enclose and secure the ends of the rod member to the screws, cap screws (not shown) can be provided through the access devices and over the rod ends. In some embodiments, the cap screws are threaded. Each cap screw can provide a downward force on a rod end, and this downward force can be transferred from the rod end to the screw head, thereby providing a secure locking mechanism for the system.

To assist in providing and securing the ends of the rod member to the screw heads, a number of different components can be provided. Among the components are a rod insertion device, an anti-torque device and a persuader device, examples of which are described below.

Rod Insertion System—Rod Insertion Device, Anti-Torque Device and Persuader Device A rod insertion system is provided that can assist in the delivery of a rod implant to a desired location within a patient. The rod insertion system can include a rod insertion device 110, an anti-torque device 142, and a persuader device 131.

FIGS. 9A and 9B illustrate a rod insertion device 110 according to embodiments of the present application. The rod insertion device 110 includes a distal gripping end 115, a sliding sleeve 118, a torque driven locking cap 121 and a handle 130.

The rod insertion device 110 includes a distal gripping end 115 for gripping a rod member so that it can be delivered into a patient. The gripping end 115 can be affixed to a shaft member of the rod insertion device 110. The shaft member can have a longitudinal axis that runs a length between the gripping end 115 and the handle 130. The distal gripping end 115 comprises two or more gripping elements (e.g., fingers or tines) that can be used to grip and hold a rod member. The gripping elements can be tapered. The gripping elements can also be compressible so as to securely grip a rod member to allow for delivery of the rod member into a patient. In some embodiments, the gripping elements are compressed by sliding the sliding sleeve 118 downward over a portion of the gripping end 115.

The sliding sleeve 118 can be located over a portion of the shaft member attached to the gripping end 115. The sliding sleeve 118 can be slidable relative to the inner shaft member. In some embodiments, upon sliding the sleeve 118 distally over a portion of the gripping end 115, the gripping end 115 can be compressed. When the gripping end 115 is compressed, it can grip or grasp a rod member or other implant. In some embodiments, the sliding sleeve 118 is actuated by rotating an adjacent torque driven locking cap 121.

The torque driven locking cap 121 is provided adjacent the sliding sleeve 118 on the rod insertion device 110. The torque driven locking cap 121 can work similar to the lock nut 80; that is, it can be rotated clockwise until it contacts and secures the sliding sleeve 118 in a position whereby the gripping end 115 is compressed. In some embodiments, the torque driven locking cap 121 includes a knurled exterior surface that allows for easier gripping.

At the proximal end of the rod insertion device 110 is a handle 130. The handle can include dimples or grooves to allow for easy handling of the rod insertion device 110.

In some embodiments, the rod insertion device 110 in FIGS. 9A and 9B can be used to deliver a rod implant adjacent to the sidewalls of an access device 5. In other embodiments, the rod insertion device 110 can be used to deliver a rod implant through an incision in a mini-open procedure between two access devices.

FIGS. 10A and 10B illustrate an anti-torque device 142 and rod persuader device 131 in use together according to embodiments of the present application. As shown in the figures, the anti-torque device 142 can be placed over the outer sleeve of the access devices, while the rod persuader device 131 can be placed above the anti-torque device and over a proximal threaded portion of the inner sleeve 21. In some embodiments, either one or both of these instruments are optional.

FIGS. 11A-11G illustrate different views of an anti-torque device 142 according to embodiments of the present application. The anti-torque device 142 comprises a handle 143 operably connected to a cannula 145. In some embodiments, the cannula 145 is configured to operate over the outer sleeve 21 of the access device 5. At the distal end of the cannula 145 is a slot 149 that can interact with a rod member that has been inserted in a patient but is not in a proper position. In some embodiments, the slot 149 of the anti-torque device can press down against the rod member, thereby helping to force the rod member into a desired position within a patient. In some embodiments, the slot forms a half-circle with a radius of between about 0.1 cm and 0.5 cm, or between about 0.3 cm and 0.4 cm.

The anti-torque device 142 can provide a number of advantages. One advantage of the anti-torque device 142 is that it can act as a persuader to force a rod member into a desired position within a patient, as noted above. Another advantage of the anti-torque device 142 is that it can provide an anti-torque mechanism that resists rotation of the access device 5 when adjusting the position of a rod member. For example, when trying to adjust the rod member into a desirable position, the anti-torque device 142 can help to ensure that the access device 5 is not rotated. In addition, in some embodiments, the distal end of the anti-torque device 142 preferably helps to hold the screw 90 in a secure position while a cap screw is tightened over a rod member and screw head.

Figure 12A:
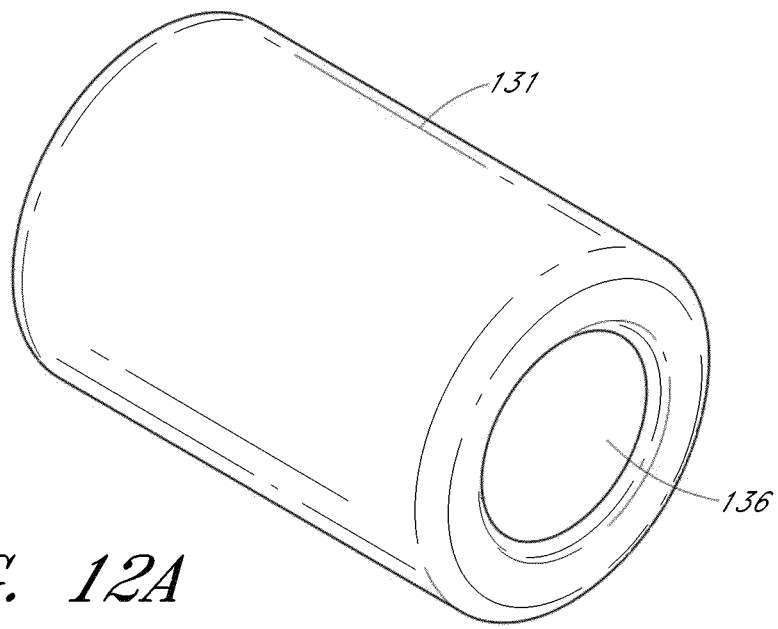
FIGS. 12A and 12B illustrate different views of a rod persuader device according to embodiments of the present application.
Figure 12B:
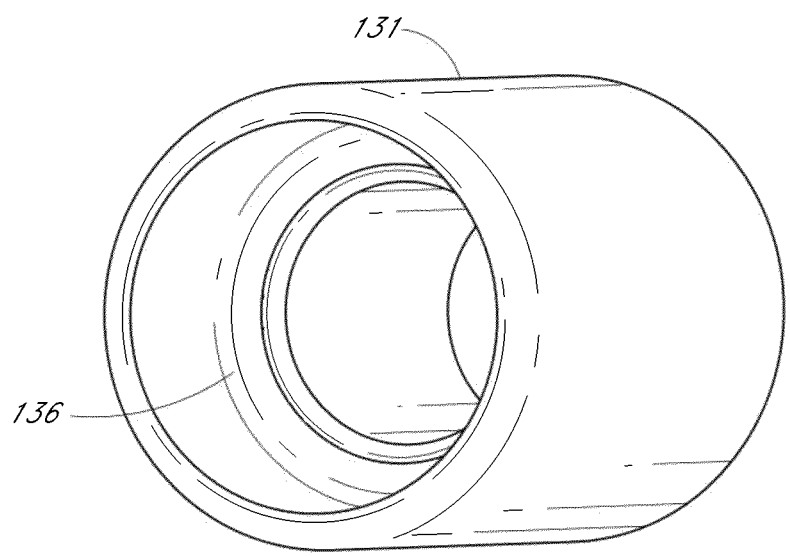

FIGS. 12A and 12B illustrate different views of a rod persuader device 131 that is configured to fit above the anti-torque device 142 and over a threaded portion of the inner sleeve 22 of the access device 5. In some embodiments, the rod persuader device 131 comprises a substantially cylindrical member that includes a hollow interior 136. In some embodiments, the rod persuader device 131 can included internal threads (not shown) which are capable with mating with the threaded portion of the inner sleeve 22. The rod persuader device 131 can be configured to be placed in contact with the anti-torque device 142 by rotating the persuader device 131 clockwise down the exposed threaded portion of the inner sleeve 22. The rod persuader device 131 can apply a downward force on the anti-torque device 142, which can then transfer to a rod member. This force helps to advantageously stabilize the rod member and place it in a desirable position within the patient's body. The rod persuader device 131 is also advantageous in that it is clearly visible outside of the patient's body, and provides a comfortable means to transmit force to stabilize and position the rod member.

In some embodiments, the persuader device 131 is optional, and can be used on its own or with the anti-torque device 142 to force a rod member into a desired location within an access device 5 (e.g., onto a seat of a screw head). In some embodiments, the anti-torque device 142 and/or persuader device 131 can be used to displace blocking tissue that may prevent the rod member from being placed in a desired location. Both the anti-torque device 142 and persuader device 131 are uniquely configured such that they can be used on top of the access device 5. This configuration allows a user (e.g., surgeon) of the anti-torque device and/or persuader device 131 to displace tissue and deliver the rod member into its proper position with ease, as the user would only have to apply relatively minor force to rotate the persuader device to interact with the anti-torque device. In addition, in some embodiments, the anti-torque device 142 and/or persuader device 131 includes an upper viewing window, such that the user can easily visualize tissue and rod member position within the access device 5.

Methods of Using the Access Device and Rod Insertion System

A procedure for using the minimally invasive access device according to embodiments of the present application will now be described. The procedure makes use of a first minimally invasive tower access device and a second minimally invasive tower access device. The access device includes an outer sleeve slidable relative to an inner sleeve, as well as a lock nut. The inner sleeve includes a pair of compressible grasping elements each having an internal protruding member to be received in an aperture of a screw head.

The first access device is provided with its distal grasping elements in an uncompressed state. A first screw having a screw head with apertures is also provided. The first screw can be placed such that its screw head is in between the uncompressed grasping elements. The access device can be attached to the screw head by compressing the grasping elements. The grasping elements are compressed by sliding the outer sleeve relative to the inner sleeve, and rotating the lock nut clockwise down a threaded portion of the inner sleeve. Upon compression of the grasping elements, the internal protruding members of the inner sleeve will be inserted into corresponding apertures of the screw head, thereby coupling the access device to the screw.

After coupling the access device to the screw, a screw driver can be provided. The screw driver, which includes a handle portion and a shaft portion, can be delivered down the access device until the shaft portion is in contact with the head of the screw. The coupled access device and screw, as well as the screw driver, are ready to be delivered through an incision.

In some embodiments, an incision of a desirable size is formed by providing a k-wire or guidewire that guides a dilator. The dilator includes one or more expandable sleeves, and can assist in providing an opening of a desirable size for inserting the coupled access device and screw into a patient.

The coupled access device and screw can be percutaneously delivered to a location (e.g., using a k-wire) such that the screw can be driven into a bone (e.g., a pedicle). The screw driver can provide rotational and axial driving forces to drive the screw into bone. Once the screw is driven into the bone, the screw driver can be removed. The access device remains coupled to the screw such that a portion of the access device remains accessible to a surgeon from outside of the patient.

A second access device can now be provided, along with a second screw. All of the steps above—coupling the access device to the screw, inserting a screw driver in the access device, delivering the coupled access device and screw to a location within a patient through an incision, driving the screw into a bone member, and removing the screw driver to leave only the coupled access device and screw—can be repeated with respect to the second access device.

A rod member can now be provided which will serve as a connecting, stabilizing member between the first and second screws. The rod member can be delivered using a rod insertion device. The rod member can be delivered along the outer sidewall of the first access device. The rod member can be delivered at an angle such that its first end is received into a distal slot of the first access device. The rod member can then be directed such that its second end is received into a distal slot of the second access device. The first end of the rod member can then be connected to the first screw within the first access device, while the second end of the rod member can then be connected to the second screw within the second access device. A screw cap can then be delivered down each of the access sleeves, and can be used to impart a downward force on the rod member to secure the rod member in the spinal stabilization system.

To ensure proper placement of the rod member within the access sleeves, an optional anti-torque device can be provided. The anti-torque device includes a cannula having a slot. The cannula can be placed over either the first or second access devices, and the slot on the cannula can be used as a persuader to force the rod member into a desired position within the patient. Simultaneously, while serving as a persuader, the anti-torque device can also limit undesirable rotation of the access devices that can be caused during adjustment of the rod member. In some embodiments, the anti-torque device helps to secure the screw in position while a screw cap imparts a downward force on the rod member that transfers to the screw head.

In addition to the anti-torque device, an optional rod persuader device can also be provided to interact with the anti-torque device. The rod persuader device can be placed above the anti-torque device, and can be inserted over a threaded portion of the inner sleeve. The anti-torque device and persuader device can help to displace tissue that may block the proper placement of the rod member within an access device. The anti-torque device and persuader device can help to force the ends of the rod members into a seat of the first and second screw heads, thereby creating a spinal stabilization member between the two screws.

Once the rod member is placed in a desired position between the two screws (e.g., either with or without the anti-torque device and/or persuader device), screw caps can be provided down the access devices that secure the ends of the rod member to the heads of the screws. Once the screw caps are provided, the first and second access devices can be removed. Alternatively, the first or second access devices can be kept in place so that the steps above can be repeated using additional devices. It would then be possible to provide additional rod implants across bone members, thereby creating a spinal stabilization system. In some embodiments, a spinal stabilization system comprises two, three, four, or more rod implants.

Once the access devices are removed, the patient can then be allowed to heal. Advantageously, with the use of the access devices described herein, the recovery time is reduced compared to conventional surgeries due to the relatively minimal incisions needed to perform the surgery.

Additional Embodiments of Devices

In addition to the embodiments of devices described above that can be used with minimally invasive surgeries, other devices are described that can also be used to assist in spinal stabilization. Many of these devices can be used with open or mini-open surgeries, as will be discussed below.

Figure 13A:
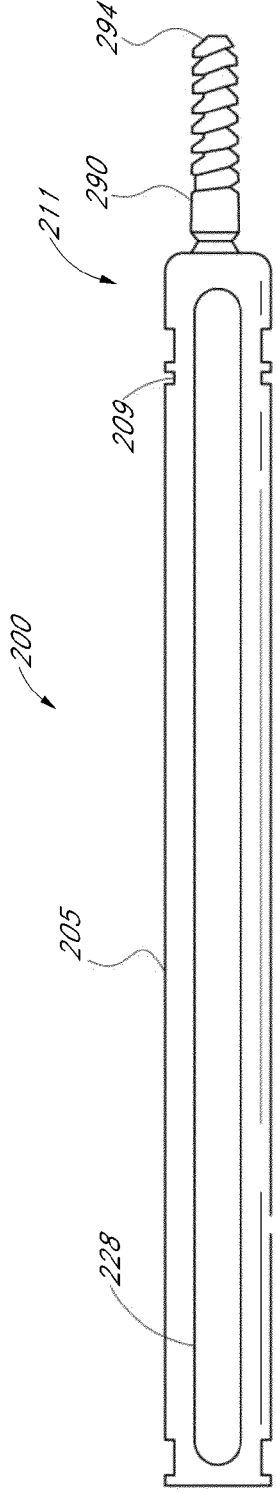
FIGS. 13A-13C illustrate a break-away screw delivery device according to embodiments of the present application.
Figure 13B:
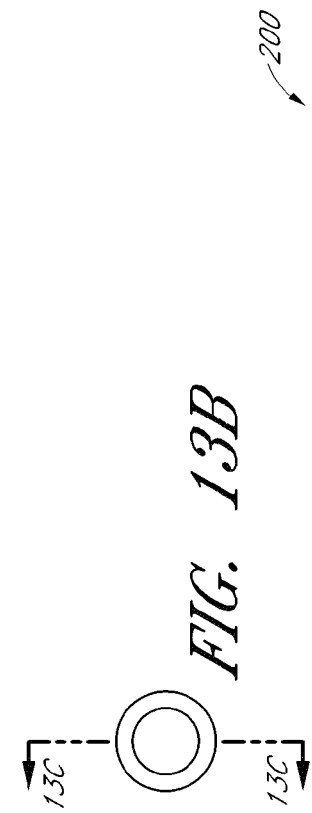
Figure 13C:
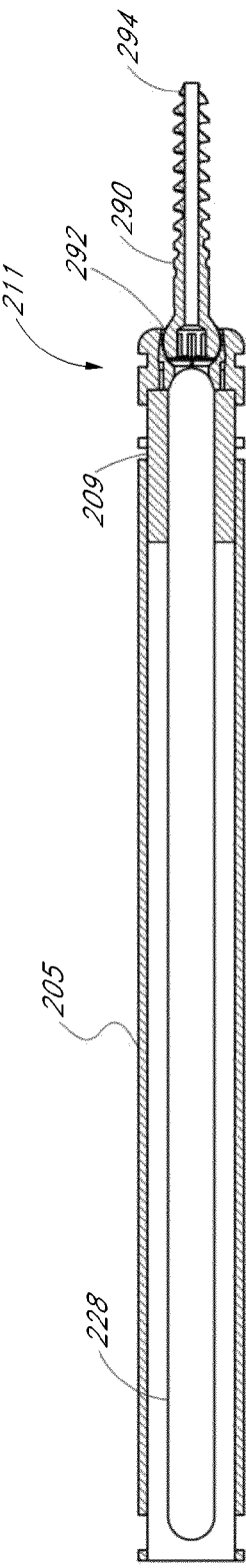
Figure 14A:
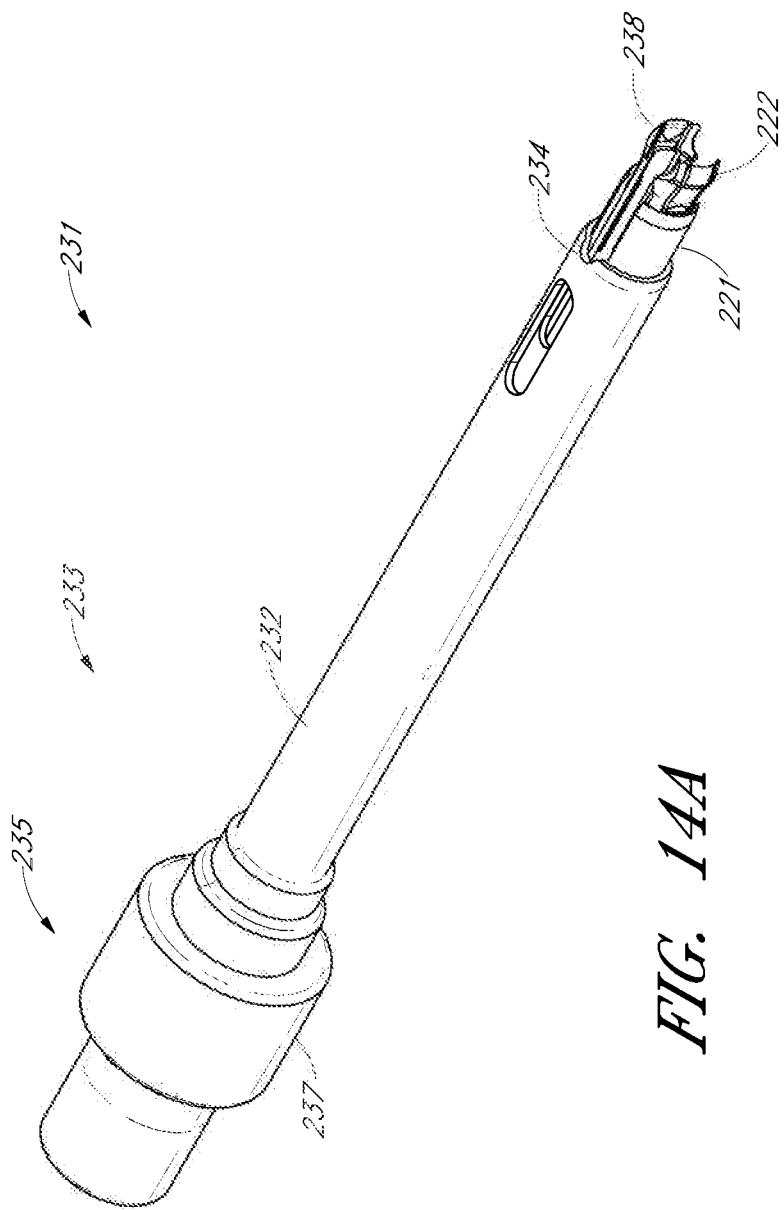

FIGS. 13A and 13B illustrate a break-away screw delivery device according to embodiments of the present application. The break-away screw delivery device 200 comprises an elongated portion 205 having an elongated slot 228. Along the length of the device 200 are grooves or indentations 209 that help to identify and facilitate break-away points as will be discussed below. The elongated portion 205 is connected to a screw portion 290 which includes a shaft 294.

In some embodiments, the break-away screw delivery device 200 can be used on its own to deliver a screw portion 290 into a bone member. While it is possible that the device 200 can be used percutaneously, the device 200 can also be used in an open surgery or mini-open surgical procedure. In operation, the device 200 can be delivered to a location within a patient's body. When the device 200 is at a desirable location, the screw portion 290 can be driven into a bone member. In some embodiments, the screw portion 290 is driven into a bone member by providing a screw driver through the interior of the delivery device 200. Once the screw portion 290 is driven into a bone member, a rod member can be inserted into the delivery device 200. The rod member can be used as a connection in between two or more delivery devices 200. Afterwards, a screw cap can be provided to secure the rod member.

Advantageously, at any time, a portion of the elongated portion 205 of the delivery device 200 can be broken off or snapped off, for example, proximate to the indentation 209. When a portion of the elongated portion 205 is snapped off, a distal end 211 of the elongated portion 205 remains. The distal end 211 resembles the head of a screw and can securely receive a stabilizing rod implant. In some embodiments, a portion of the elongated portion 205 is snapped off after driving the screw portion 290 into a bone, delivering a rod member and providing a secure screw cap. The snapped off portion of the elongated portion 205 can be removed, thereby leaving within the patient a part of a bone stabilizing system.

FIGS. 14A-14H illustrate different views of an alternate persuader system according to embodiments of the present application. Like the break-away screw delivery device 200, the persuader system 231 can be used in an open procedure or mini-open procedure. The persuader system 231 includes a persuader sleeve 233 that is operably connected to an inner sleeve 222 having grasping elements 238 and an outer sleeve 221. The inner sleeve 222 and outer sleeve 221 can be slidable relative to one another. The persuader sleeve 233 further includes a proximal portion 235 having a handle 237 that serves as an actuating element and a distal portion 232 having a cut-out portion 234.

In some embodiments, the persuader system 231 can be used to deliver an implant, such as a rod member, to a desirable location in a patient during open surgery. The persuader system 231 can include an inner sleeve 222 and outer sleeve 221 that are slidable relative to one another. The sleeves can operate similarly to the inner sleeve and outer sleeve of the access device described above in that sliding the sleeves relative to one another can result in compression of the grasping elements 238, thereby allowing a rod implant to be grasped therebetween. Once a rod implant is grasped, the persuader system 231 can be delivered to a desirable location within a patient. In some embodiments, by actuating the handle 237 of the persuader system (e.g., by rotation), the distal portion 232 of the persuader system can be extended until the cut-out portion 234 is in contact with the rod member. Advantageously, the cut-out portion 234 can help to stabilize and secure the rod member in a desirable position within the patient.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A system for spinal stabilization, comprising:
a percutaneous access device including:
an outer sleeve having a proximal slot and a distal slot;
an inner sleeve having a proximal section and a distal section, the proximal section being operably connected to a spring latch having a tab member, the proximal section including a threaded portion, the distal section including a slot and a pair of compressible grasping elements, each of the grasping elements including slits, an internal tapered surface, and an internal protruding member capable of being received in an aperture in a head of a screw member, wherein the inner sleeve is configured to be slidably received into the outer sleeve such that the spring latch is located within the proximal slot of the outer sleeve and the slot of the inner sleeve is aligned with the distal slot of the outer sleeve; and
a lock nut having an internal engagement surface for engaging the threaded portion of the inner sleeve, wherein placement of the lock nut at a bottom section of the threaded portion of the inner sleeve results in compression of the grasping elements, and wherein the internal engagement surface is configured to interact with the tab member via depressions to limit counter rotation of the lock nut during use;
a cannulated screw member attachable to the inner sleeve, the cannulated screw member comprising a head portion coupled to a shaft, wherein the head portion includes a seat for receiving a rod member, one or more apertures for receiving the internal protruding member of the inner sleeve, and at least one slot for interacting with the internal tapered surface of the inner sleeve;
a screw driver for rotating and driving the screw member into a bone;
a rod insertion device including a handle and a distal gripping end for gripping and delivering a rod member;
an anti-torque device including a handle connected to a cannula, wherein the cannula is configured to be placed over the outer sleeve, and wherein the cannula includes a side slot for engaging the rod member; and
a persuader device that can interact with the anti-torque device and assist in forcing the rod member into the seat of the screw member, the persuader device having a hollow interior and internal threads.

2. A system for spinal stabilization, comprising:
an outer sleeve having a distal slot; and
an inner sleeve having a proximal section and a distal section, the proximal section including a threaded portion, the distal section including a slot and a pair of compressible grasping elements, each of the grasping elements including an internal protruding member;
wherein the inner sleeve is configured to be slidably received into the outer sleeve such that the slot of the inner sleeve is aligned with the distal slot of the outer sleeve, and wherein sliding the outer sleeve relative to the inner sleeve actuates compression of the grasping elements of the inner sleeve;
an anti-torque device comprising a cannula, wherein the cannula is configured to be placed over the outer sleeve, the cannula having a slot configured to engage a rod member; and
a persuader device having a hollow interior and internal threads configured to engage the threaded portion of the inner sleeve;
wherein the anti-torque device is placed over the outer sleeve, the persuader device is threaded onto the threaded portion of the inner sleeve such that the persuader device is in contact with the anti-torque device, and the persuader device is configured to rotate relative to the anti-torque device, to force the anti-torque device against the rod member.

3. The system of claim 2, further comprising a lock nut having an internal engagement surface for engaging the threaded portion of the inner sleeve.

4. The system of claim 3, wherein placement of the lock nut at a bottom section of the threaded portion of the inner sleeve results in compression of the grasping elements.

5. The system of claim 2, further comprising a cannulated screw member attachable to the inner sleeve including a head portion affixed to a shaft, wherein the head portion includes a pair of apertures for receiving the internal protruding member of each of the grasping elements.

6. The system of claim 2, further comprising a rod insertion device including a handle and a distal gripping end for gripping and delivering a rod member near the outer sleeve.

7. The system of claim 2, further comprising a spring latch operably connected to the proximal section of the inner sleeve.

8. The system of claim 7, wherein the spring latch is insertable within a proximal slot of the outer sleeve.

9. The system of claim 7, wherein the spring latch includes a marker for identifying a mode of operation of the percutaneous access device.

10. The system of claim 7, wherein the spring latch includes a tab member for interacting with a lock nut to limit loosening of the lock nut.

11. The system of claim 2, wherein the distal slot of the outer sleeve and the slot of the inner sleeve are of substantially the same width.

12. The system of claim 2, wherein the compressible grasping elements include slits.

13. The system of claim 2, wherein the inner sleeve is configured to be received into a hollow interior of the outer sleeve.

14. The system of claim 2, wherein the slot of the inner sleeve is about half the length of a non-threaded portion of the inner sleeve.

15. A system for spinal stabilization, comprising:
an access device comprising an elongate sleeve having a proximal section and a distal section, the proximal section including a threaded portion, the distal section including a slot and a having a distal end configured to grasp a screw, wherein the slot extends from the distal end toward a proximal end of the elongate sleeve, wherein the slot is configured to allow passage of a rod member therethrough;
an anti-torque device comprising a cannula configured to be placed over the access device and a handle operatively connected to the cannula proximate a proximal end of the cannula, wherein a distal end of the cannula includes a side slot for engaging the rod member; and a persuader device having a hollow interior and internal threads configured to engage the threaded portion of the access device;

wherein the anti-torque device is placed over the access device, the persuader device is threaded onto the threaded portion of the access device such that the persuader device is in contact with the anti-torque device, and the persuader device is configured to rotate relative to the anti-torque device and the access device to apply a downward force on the anti-torque device to apply a downward force on the rod member.

16. The system of claim 15, wherein the distal end of the elongate sleeve comprises two compressible grasping elements configured to grasp the screw.

17. The system of claim 16, wherein the grasping elements comprise one or more longitudinal slits configured to enhance compressibility of the grasping elements.

18. The system of claim 17, wherein each grasping element comprises two longitudinal slits extending from the distal end of the elongate sleeve toward the proximal end such that each grasping element is divided into three sections.

19. The system of claim 15, further comprising an outer sleeve configured to slidably receive the elongate sleeve.

20. The system of claim 19, wherein when the elongate sleeve is slidably received within the outer sleeve, distal movement of the outer sleeve relative to the elongate sleeve causes compression of the grasping elements.

* * * * *